United States Patent
Sladek et al.

Patent Number: 5,604,115
Date of Patent: Feb. 18, 1997

[54] LIVER ENRICHED TRANSCRIPTION FACTOR

[75] Inventors: Frances M. Sladek, Riverside, Calif.; Weimin Zhong, New York; James E. Darnell, Jr., Larchmont, both of N.Y.

[73] Assignee: The Rockefeller University, New York, N.Y.

[21] Appl. No.: 78,222

[22] PCT Filed: Dec. 23, 1991

[86] PCT No.: PCT/US91/09733

§ 371 Date: Oct. 28, 1993

§ 102(e) Date: Oct. 28, 1993

[87] PCT Pub. No.: WO92/11365

PCT Pub. Date: Sep. 7, 1992

[51] Int. Cl.$^6$ .......................... C12P 21/06; C12N 15/09; C12N 15/12; C12N 15/63

[52] U.S. Cl. ................ 435/69.1; 435/252.3; 435/254.11; 435/320.1; 435/325; 435/348; 536/23.5

[58] Field of Search .......................... 435/69.1, 320.1, 435/252.33, 240.1, 252.3, 254.11; 536/23.5

[56] References Cited

U.S. PATENT DOCUMENTS 4,394,443  7/1983  Weissman et al. .................... 435/6

OTHER PUBLICATIONS

Ahe, von der D., Janich, S., Scheidereit, C., Renkawitz, R., Schutz, G., and Beato, M. (1985). Glucocorticoid and progesterone receptors bind to the same sites in two hormonally regulated promoters. *Nature*, 313, 706–709.

Baumhueter, S., Mendel, D. B., Conley, P. B., Kuo, C. J., Turk, C., Graves, M. K., Edwards, C. A., Courtois, G., and Crabtree, G. R. (1990). HNF–1 shares three sequence motifs with the POU domain proteins and is identical to LF–B1 and APF. *Genes and Development* 4, 372–379.

Beato, M. (1989). Gene regulation by steroid hormones. *Cell* 56, 335–344.

Bell, J. Ellis, 1988, Protein Purification: Affinity Chromatograpy. *Proteins and Enzymes* Prentice–Hall Inc.. 45–63.

Birkenmeier, E. H., Gwynn, B., Howard, S., Jerry, J., Gordon, J. I., Landschulz, W. H., and McKnight, S. L. (1989). Tissue–specific expression, developmental regulation and mapping of the gene encoding CCAAT/enhancer binding protein. *Genes and Development*, 3, 1146–1156.

Brand, N., Petkovich, M., Krust, A., Chambon, P., de The, H., Marchio, A., Tiollais, P., and Dejean, A. (1988). Identification of a second human retinoic acid receptor. *Nature*, 332, 850–853.

Briggs, M. R., Kadonaga, J. T., Bell, S. P., and Tjian, R. (1986) Purification and biochemical characterization of the promoter–specific transcription factor, Sp1. *Science*, 234, 47–52.

(List continued on next page.)

*Primary Examiner*—Robert A. Wax
*Assistant Examiner*—Kawai Lau
*Attorney, Agent, or Firm*—Klauber & Jackson

[57] ABSTRACT

HNF-4 (hepatocyte nuclear factor 4) is a protein enriched in liver extracts that binds to sites required for the transcription of the transthyretin (TTR) and apolipoprotein CIII (apoCIII) genes (Costa et al., 1989; Costa et al., 1990; Leff et al., 1989). We have purified HNF-4 protein (54 kD) and isolated a cDNA clone encoding the protein. HNF-4 is a member of the steroid hormone receptor superfamily with an unusual amino acid in the conserved "knuckle" of the first zinc finger (DGCKG). This and the fact that HNF-4 does not bind significantly to estrogen, thyroid hormone or glucocorticoid response elements indicate that HNF-4 may represent a new subfamily. HNF-4 binds to its recognition site as a dimer and activates transcription in a sequence-specific fashion in nonhepatic (HeLa) cells. HNF-4 mRNA is present in kidney and intestine as well as liver but is absent in other tissues. DNA binding data suggest that HNF-4 could be identical to liver factor A1 (LF-A1), a factor previously shown to regulate the transcription of the α-1 antitrypsin, apolipoprotein A1 and pyruvate kinase genes.

29 Claims, 19 Drawing Sheets

OTHER PUBLICATIONS

Breslow, J. (1988). Apolipoprotein genetic variation and human disease. *Physiol. Reviews*, 68, 85–132.

Capon, D. J. et al. (1989). Designing CF4 immunoadhesins for AIDS therapy. *Nature*, 337, 525–531.

Carlsson, R., and Glad, C. (Jun., 1989). Monoclonal antibodies into the '90s. *Bio/Technology*, 7, 567–573.

Cate, R. L. et al. (1986). Isolation of the bovine and human genes for Mullerian inhibiting substance and expression of the human gene in animal cells. *Cell*, 45, 685–598.

Cech, T. R. (1988). Ribozymes and their medical implications. *J. Amer. Med. Assn.*, 260, 3030–3044.

Chomczynski, P. and Sacchi, N. (1987). Single-step method of RNA isolation by acid guanidinium thiocyanate–phenol–chloroform extraction. *Anal. Biochem.*, 162, 156–159.

Costa, R. H., Lai, E., and Darnell, J. E., Jr. (1986). Transcriptional control of the mouse prealbumin (transthyretin) gene: both promoter sequences and a distinct enhancer are cell specific. *Mol. and Cell. Biol.*, 6, 4697–4708.

Costa, R. H., Grayson, D. R., Xanthopoulos, K. G., and Darnell, J. E., Jr. (1988). A liver-specific DNA–binding protein recognizes multiple nucleotide sites in regulatory regions of transthyretin, a1–antitrypsin, albumin, and simian virus 40 genes. *Proc. Natl. Acad. Sci.*, 85, 3840–3844.

Costa, R. H., Grayson, D. R. and Darnell, J. E. Jr. (1989). Multiple hepatocyte–enriched nuclear factors function in the regulation of transthyretin and a1–antitrypsin genes. *Mol. and Cell. Biol.*, 9, 1415–1425.

Costa, R. H., Van Dyke, T. A., Yan, C., Kuo, F., and Darnell, J. E., Jr. (1990). Similarities in transthyretin gene expression and differences in transcription factors: liver and yolk sac compared to choroid plexus. *Proc. Natl. Acad. Sci. USA*, 87, 6589–6593.

Courtois, G., Morgau, J. G., Campbell, L. A., Fourel, G. and Crabtree, G. R. (1987). Interaction of a liver-specific nuclear factor with the fibrinogen and al–antitrypsin promoters. *Science*, 238, 688–692.

Danielsen, M., Hinck, L., and Ringold, G. M. (1989). Two amino acids within the knuckle of the first zinc finger specify DNA response element activation by the glucocorticoid receptor. *Cell*, 57, 1131–1138.

Davis, M. M. (1986). Subtractive cDNA hybridization and the T–cell receptor gene. *Handbook of Experimental Immunology in Four Volumes*, 4th ed. Blackwell Scientific Publications, Oxford, England, 76.1–76.13.

Davis, M. M. et al. (1984). Cell type–specific cDNA probes and the murine I region: The localization and orientation of ad. *Proc. Natl. Acad. Sci. USA*, 81, 2194–2198.

Derman, E., Krauter, K., Walling, L., Weinberger, C., Ray, M. and Darnell, J. E. Jr. (1981). Transcriptional control in the production of liver-specific mRNAs. *Cell*, 23, 731–739.

de The, H., Marchio, A., Tiollais, P., and Dejean, A. (1987). A novel steroid thyroid hormone receptor–related gene inappropriately expressed in human hepatocellular carcinoma. *Nature*, 330, 667–670.

Duguid, J. R. et al. (1988). Isolation of cDNAs of scrapie–modulated RNMAs by subtractive hybridization of cDNA library. *Proc. Natl. Acad. Sci. USA*, 85, 5738–5742.

Evans, R. M. (1988). The steroid and thyroid hormone receptor superfamily. *Science*, 240, 889–895.

Fawell, S. E., Lees, J. A., White, R. and Parker, M. G. (1990). Characterization and colocalization of steroid binding and dimerization activities in the mouse estrogen receptor. *Cell*, 60, 953–962.

Feinberg, A. P., and Vogelstein, B. (1983). A technique for radiolabeling DNA restriction endonuclease fragments to high specific activity. *Anal. Biochem.*, 132, 6–13.

Fisher, R. A. et al. (1988). HIV infection is blocked in vitro by recombinant soluble CD4. *Nature*, 331, 76–78.

Forman, B. M., Yan, C. R., Au, M., Casanova, J., Ghysdael, J., and Samuels, H. H. (1989). A domain containing leucine–zipper–like motifs mediate novel in vivo interactions between the thyroid hormone and retinoic acid receptors. *Mol. End.*, 3, 1610–1626.

Forman, B. M. and Samuels, H. H. (1990). Interactions among a subfamily of nuclear hormone receptors: The regulatory zipper model. *Mol. End.* 4, 1293–1301.

Frain, M., Swart, G., Monaci, P., Nicosia, A., Stampfli, S., Frank, R., and Cortese, R. (1989). The liver–specific transcription factor LF–Bl contains a highly diverged homeobox DNA binding domain. *Cell*, 59, 145–157.

Fried, M. and Crothers, D. M. (1981). Equilibria and kinetics of lac repressor–operator interactions by polyacrylamide gel electrophoresis. *Nucleic Acids Res.*, 9, 6505–6525.

Giguere, V., Yang, N., Segui, P., and Evans, R. M. (1988). Identification of a new class of steroid hormone receptors. *Nature*, 331, 91–94.

Glass, C. K. Holloway, J. M., Devary, O. V., and Rosefeld, M. (1988) The thyroid hormone receptor binds with opposite transcription effects to a common sequence motif in thyroid hormone and estrogen response elements. *Cell*, 54: 313–323.

Glass, C. K., Lipkin, S. M., Devary, O. V., and Rosenfeld, M. G. (1989). Positive and negative regulation of gene transcription by a retinoic acid–thyroid hormone receptor heterodimer. *Cell*, 59, 697–708.

Gorman, C. M., Moffat, L. F. and Howard, B. H. (1982). Recombinant genomes which express chloramphenicol acetyltransferase in mammalian cells. *Mol. Cell. Biol.*, 2, 1044–1051.

Gorman, C. M., Howard, B. H. and Reeves R. (1983). Expression of recombinant plasmids in mammalian cells is enhanced by sodium butyrate. *Nucleic Acids Res.*, 11, 7631–7648.

Gorski, K., Carneiro, M. and Schibler, U. (1986). Tissue–specific in vitro transcription from the mouse albumin promoter. *Cell*, 47, 767–776.

Green, N., Alexander, H., Olson, A., Alexander, S., Shinnick, T. M., Sutcliffe, J. G., and Lerner, R. A. (1982). Immunogenic structure of the influenza virus hemagglutinin. *Cell*, 28, 477–487.

Green, S., Walter, P., Kumar, V., Krust, A., Bornert, J. M., Argos, P., and Chambon, P. (1986). Human oestrogen receptor cDNA: Sequence, expression and homology to c/epb. *Nature*, 320, 134–139.

Green, S. and Chambon, P. (1988). Nuclear receptors enhance our understanding of transcription regulation. *Trends Genet.*, 4, 309–314.

Gubler, U., and Hoffman, B. J. (1983). A simple and very efficient method for generating cDNA libraries. *Gene*, 25, 263–269.

Hamada, K., Gleason, S. L., Levi, B. Z., Hirschfeld, S., Appella, E., and Ozato, K. (1989). H–2RIIBP, a member of the nuclear hormone receptor superfamily that binds to both the regulatory element of major histocompatibility class I genes and the estrogen response element. *Proc. Natl. Acad. Sci. USA*, 86, 8289–8293.

Hambor, J. E. et al. (1988). Functional consequences of antisense RNA-mediate inhibition of CD8 surface expression in a human T cell clone. *J. Exp. Med.*, 168, 1237–1245.

Hardon, E. M., Frain, M., Paonessa, G. and Cortese, R. (1988). Two distinct factors interact with the promoter regions of several liver–specific genes. *The EMBO J.*, 7, 1711–1719.

Haseloff, J., and Gerlach, W. L. (1988). Simple RNA enzymes with new and highly specific endoribonuclease activities. *Nature*, 334, 585–591.

Hedrick, S. M. et al. (1984). Isolation of cDNA clones encoding T cell–specific membrane–associated proteins. *Nature*, 308, 149–153.

Ito, Y., Azrolan, N., O'Connell, A., Walsh, A., and Breslow, J. L. (1990) Hypertriglyceridemia as a result of human apoCIII gene expression in transgenic mice. *Science*, 249, 790–793.

Johnson, P. F., Landschulz, W. H., Graves, B. J., and McKnight, S. L. (1987). Identification of a rat liver nuclear protein that binds to the enhancer core element of three animal viruses. *Genes and Development*, 1, 133–146.

Johnson, P. F., (1990). Transcriptional activators in hepatocytes. In *Cell Growth and Differentiation*, 1, 47–52.

Kadonaga, J. T., and Tjian, R. (1986). Affinity purification of sequence–specific DNA binding proteins. *Proc. Natl. Acad. Sci. USA*, 83, 5889–5893.

Kennedy, R. C. et al. (Jul. 1986). Anti–idiotypes and immunity. *Sci. Am.*, 255, 48–56.

Klein–Hitpab, L., Schorpp, M., Wagner, U., and Ryffel, G. U., (1986). An estrogen–responsive element derived from the 5' flanking region of the Xenopus vitellogenin A2 gene functions in transfected human cells. *Cell*, 46, 1053–1061.

Kozak, M. (1987). An analysis of 5'–noncoding sequences from 699 vertebrate messenger RNA's. *Nucleic Acids Res.*, 15, 8125–8143.

Krebs, E., Eisenman, R., Kuenzel, E., Litchfield, D., Lozeman, F., Lischer, B. and Sommercorn, J. (1988). Casein kinase II as a potentially important enzyme concerned with signal transduction. In *Molecular Biology of Signal Transduction*. (Cold Spring Harbor Laboratory), pp. 77–84.

Kumar, V., and Chambon, P. (1988). The estrogen receptor binds tightly to its responsive element as a ligand–induced homodimer. *Cell*, 55, 145–156.

Kuo, C. F., Xanthopoulos, K. G., and Darnell, J. E. Jr. (1990). Fetal and adult localization of C/EBP: evidence for combinatorial action of transcription factors in cell–specific gene expression. *Development*, 109, 473–481.

Kuwabara, M. D. and Sigman, D. S. (1987). Footprinting DNA–protein complexes in situ following gel retardation asays using 1, 10–phenathroline–copper ion: *Escherichia coli* RNA polymerase–lac promoter complexes. *Biochem.*, 26, 7234–7238.

Laemmli, U. K. (1970). cleavage of structural proteins during the assembly of the head of bacteriaphage T4. *Nature*, 227, 680–685.

Lai, E., Prezioso, V. R., Smith, E., Litvin, O., Costa, R. H., and Darnell, J. E., Jr. (1990). HNF–3A, a hepatocyte–enriched transcription factor of novel structure is regulated transcriptionally. *Genes and Development*, 4, 1427–1436.

Landschulz, W. H., Johnson, P. F., Adashi, E. Y., Graves, B. J., and McKnight, S. L. (1988). Isolation of a recombinant copy of the gene encoding C/EBP. *Genes and Development*, 2, 786–800.

Lathe, E. (1985). Synthetic oligonucleotide probes deduced from amino acid sequence data: Theoretical and practical considerations. *J. Mol. Biol.*, 183, 1–12.

Leff, T., Reue, K., Melian, A., Culver, H., and Breslow, J. L. (1989). A regulatory element in the ApoCIII promoter that directs hepatic specific transcription binds to proteins in expressing and nonexpressing cell types. *J. Biol. Chem.*, 264, 16132–16137.

Lew, D. J., Decker, T., Strehlow, I. and Darnell, J. E. (1990). Overlapping elements in the GBP gene promoter mediate transcriptional induction by alpha and gamma–interferon. *Mol. Cell Biol.*, in press.

Li, Y., Shen, R.–F., Tsai, S. Y., and Woo, S. L. C. (1988). Multiple hepatic trans–acting factors are required for in vitro transcription of the human alpha–1–antitrypsin gene. *Mol. and Cell. Biol.*, 8, 4362–4369.

MacGregor, G. R., and Caskey, C. T. (1989). Construction of plasmids that express *E. coli* b–galactosidase in mammalian cells. *Nucleic Acids Res.*, 17, 2365.

Mader, S., Kumar, V., de Verneuil, H., and Chambon, P. (1989). Three amino acids of the oestrogen receptor are essential to its ability to distinguish an oestrogen from a glucocorticoid–responsive element. *Nature*, 338, 271–274.

Mangelsdorf, D. J., Ong, E. S., Dyck, J. A. and Evans, R. M. (1990). Nuclear receptor that identifies a novel retinoic acid response pathway. *Nature*, 345, 224–229.

Marcus–Sekura, C. J. (1988). Techniques for using antisense oligonucleotides to study gene expression. *Anal. Biochem.*, 172, 289–295.

Matsudaira, P. (1987). Sequence from picomole quantities of proteins electroblotted onto polyvinylidene difluorid membranes. *J. Biol. Chem.*, 262, 10035–10038.

McKnight, G. S., and Palmiter, R. D. (1979). Transcriptional regulation of the ovalbumin and conalbumin genes by steroid hormones in chick oviduct. *J. Biol. Chem.*, 254, 9050–9058.

Mermod, N., O'Neill, E. A., Kelly, T. J. and Tjian, R. (1989). The proline–rich transcriptional activator of CTF/NF–1 is distinct from the replication and DNA binding domain. *Cell*, 58, 741–753.

Milstein, C., *Handbook of Experimental Immunology* Overview: monoclonal antibodies. Chapter 107. 1–12.

Miyajiima, N., Kadowaki, Y., Fukushige, Shiminizu, S., Semba, K., Yamanashi, Y. H., Matsubara, K., Toyoshima, K., and Yamanoto, T. (1988). Identification of two novel members of erbA superfamily by molecular cloning: The gene products of the two are highly related to each other. *Nucleic Acids Res.*, 16, 11057–11074.

Monaci, P., Nicosia, A., and Cortese, R. (1988). Two different liver–specific factors stimulate in vitro transcription from the human a1–antitrypsin promoter. *The EMBO J.*, 7, 2075–2087.

Mueller, C. R., Maire, P., and Schibler, U. (1990). DBP, a liver–enriched transcriptional activator, is expressed late in ontogeny and its tissue specificity is determined posttranscriptionally. *Cell*, 61, 279–291.

Tsai, S. Y. et al. (1988). Molecular interactions of steroid hormone receptor with its enhancer element: Evidence for receptor dimer formation. *Cell*, 55, 361–369.

Pearson, W. R., and Lipman, D. J. (1988). Improved tools for biological sequence comparison. *Proc. Natl. Acad. Sci. USA*, 85, 2444–2448.

Puissant, C., and Houdebine, L. M. (1990). An improvement of the single–step method of RNA isolation by acid guanidinium thiocyanate–phenol–chloroform extraction. *BioTechniques*, 8, 148–149.

Reue, K., Leff, T., and Breslow, J. L. (1988). Human apolipoprotein CIII gene expression is regulated by positive and negative Cis–acting elements and tissue–specific protein factors. *The J. of Biol. Chem.*, 263, 6857–6864.

Rosen, C. A., Sodroski, J. G. and Haseltine, W. A. (1985). The location of cis–acting regulatory sequences in the human T cell lymphotropic virus type III (HTLV–III/LAV) long terminal repeat. *Cell*, 41, 813–823.

Ruppert, S., Boshart, M., Bosch, F. X., Schmid, W., Fournier, R. E. K., and Schutz, G. (1990). Two genetically defined trans–acting loci coordinately regulate overlapping sets of liver–specific genes. *Cell*, 61, 895–904.

Ryseck, R. P., Macdonald–Bravo, H., Mattei, M. G., Ruppert, S., and Bravo, R. (1989). Structure, mapping and expression of a growth factor inducible gene encoding a putative nuclear hormonal binding receptor. *The EMBO J.*, 8, 3327–3335.

Saiki, R. K., Gelfand, D. H., Stoffel, S., Scharf, S. J., Higuchi, R., Horn, G. T., Mullis, K. B., and Erlich, H. A. (1988). Primer–directed enzymatic amplification of DNA with a thermostable DNA polymerase. *Science*, 239, 487–491.

Sanger, F., Nicklen, S., and Coulson, A. R. (1977). DNA sequencing with chain terminating inhibitors. *Proc. Natl. Acad. Sci. USA*, 74, 5463–5467.

Sambrook, J., Fritsch, E. F., and Maniatis, T. (1989). *Molecular cloning: A laboratory manual.* (Cold Spring Harbor, N.Y.: Cold Spring Harbor Laboratory).

Sargent, T. D. (1987). Isolation of differentially expressed genes. *Methods in Enzymol.*, 152, 423–447.

Schule, R., Umesono, K., Mangelsdorf, D. J., Bolado, J., Pike, J. W., and Evans, R. M. (1990). Jun–fos and receptors for vitamins A and D recognize a common response element in the human osteocalcin gene. *Cell*, 61, 497–504.

Seed, B. (1987). An LFA–3 cDNA encodes a phospholipid–linked membrane protein homologous to its receptor CD2. *Nature*, 329, 840–842.

Seed, B., and Aruffo, A. (1987). Molecular cloning of the CD2 antigen, the T–cell erythrocyte receptor, by a rapid immunoselection procedure. *Proc. Natl. Acad. Sci. USA*, 84, 3365–3369.

Sladek, Frances M. et al., (1990). Liver–enriched transcription factor HNF–4 is a novel member of the steroid hormone receptor superfamily. *Genes & Development*, 4 No. 12b, 2235–2438.

Stahle, U., Klock, G., and Schutz, G. (1987). A DNA sequence of 15 base pairs is sufficient to mediate both glucocorticoid and progesterone induction of gene expression. *Proc. Natl. Acad. Sci. USA.*, 84, 7871–7875.

Tsai, S. Y., Carlstedt–Duke, J., Weigel, N. L., Dahlman, K., Gustafsson, J. A., Tsai, M. J., and O'Malley, B. W. (1988). Molecular interactions of steroid hormone receptor with its enhancer element: Evidence for receptor dimer formation. *Cell*, 55, 361–369.

Umesono, K., Giguere, V., Glass, C. K., Rosenfeld, M. G., and Evans, R. M. (1988). Retinoic acid and thyroid hormone induce gene expression through a common responsive element. *Nature*, 336, 262–265.

Umesono, K. and Evans, R. M. (1989). Determinants of target gene specificity for steroid/thyroid hormone receptors. *Cell*, 57, 1139–1146.

Vaulont, S., Puzenat, N., Kahn, A., and Raymondjean, M. (1989). Analysis by cell–free transcription of the liver–specific pyruvate kinase gene promoter. *Mol. and Cell. Biol.*, 9, 4409–4415.

Wang, L. H., Tsai, S. Y., Cook, R. G., Beattie, W. G., Tsai, M. J. and O'Malley, B. W. (1989). COUP transcription factor is a member of the steroid receptor superfamily. *Nature*, 340, 163–166.

Weinberger, C., Thompson, C. C., Ong, E. S., Lebo, R., Gruo, D. J., and Evans, R. M. (1986). The c/epb gene encodes a thyroid hormone receptor. *Nature*, 243, 641–646.

Wingender, E. (1990). Transcription regulating proteins and their recognition sequences. *Critical Reviews in Eukaryotic Gene Expression*, 1, 11–48.

Wysocki, L. J., and Sato, V. L. (1978). Panning for lymphocytes: A method for cell selection. *Proc. Natl. Acad. Sci. USA*, 75, 2844–2848.

Xanthopoulos, K. G., Mirkovitch, J., Decker, T., Kuo, C. F., and Darnell, J. E., Jr. (1989). Cell–specific transcriptional control of the mouse DNA–binding protein mC/EBP. *Proc. Natl. Acad. Sci. USA* 86, 4117–4121.

Xanthopoulos, K. G. et al. (1991). The different tissue transcription patterns of genes for HNF–1, C/EBP, HNF–3 and HNF–4, protein factors that govern liver–specific transcription. *Proc. Natl. Acad. Sci. USA*, 88, 3807–3811.

Yamasaki, K. et al. (1988). Cloning and expression of the human interleukin–6 (BSF–2/IFNB2) receptor. *Science*, 241, 825–828.

Young, R. A. and Davis, R. W. (1983). Efficient isolation of genes by using antibody probes. *Proc. Natl. Acad. Sci. USA*, 80, 1194–1198.

```
CGACAGGGGGCTGAGGGGTGGGTAGAGGAGAATGCGACTCTCTAAAACCCTCGCC         55

GAC ATG GAC ATG GCT GAC TAC AGT GCT GCC TTG GAC CCA GCC         97
    Met Asp Met Ala Asp Tyr Ser Ala Ala Leu Asp Pro Ala
    1           5                   10

TAC ACC ACC CTG GAG TTT GAA AAT GTG CAG GTG TTG ACC ATG         139
Tyr Thr Thr Leu Glu Phe Glu Asn Val Gln Val Leu Thr Met
    15              20                  25

GGC AAT GAC ACA TCC CCA TCT GAA GGT GCC AAC CTC AAC TCA         181
Gly Asn Asp Thr Ser Pro Ser Glu Gly Ala Asn Leu Asn Ser
        30              35                  40

TCC AAC AGC CTG GGT GTC AGT GCC CTG TGT GCC ATC TGT GGC         223
Ser Asn Ser Leu Gly Val Ser Ala Leu Cys Ala Ile Cys Gly
            45              50                  55

GAT CGG GCC ACT GGC AAA CAC TAC GGA GCC TCA AGC TGT GAC         265
Asp Arg Ala Thr Gly Lys His Tyr Gly Ala Ser Ser Cys Asp
                60              65

GGC TGC AAG GGA TTC TTC AGG AGG AGC GTG AGG AAG AAC CAC         307
Gly Cys Lys Gly Phe Phe Arg Arg Ser Val Arg Lys Asn His
70              75                  80

ATG TAC TCC TGC AGG TTT AGC AGG CAG TGC GTG GTA GAC AAA         349
Met Tyr Ser Cys Arg Phe Ser Arg Gln Cys Val Val Asp Lys
    85              90                  95

GAT AAG AGG AAC CAG TGT CGT TAC TGC AGG CTC AAG AAG TGC         391
Asp Lys Arg Asn Gln Cys Arg Tyr Cys Arg Leu Lys Lys Cys
        100             105                 110

TTC CGG GCT GGC ATG AAG AAA GAA GCC GTC CAA AAT GAG CGG         433
Phe Arg Ala Gly Met Lys Lys Glu Ala Val Gln Asn Glu Arg
            115             120                 125

GAT CGG ATC AGC ACG CGG AGG TCA AGC TAC GAG GAC ATC AGC         475
Asp Arg Ile Ser Thr Arg Arg Ser Ser Tyr Glu Asp Ile Ser
                130             135

CTA CCC TCC ATT AAT GCG CTC CTG CAG GCA GAG GTC CTG TCT         517
Leu Pro Ser Ile Asn Ala Leu Leu Gln Ala Glu Val Leu Ser
140             145                 150

CAG CAG ATC ACC TCC CCC ATC TCT GGG ATC AAT GGC GAC ATT         559
Gln Gln Ile Thr Ser Pro Ile Ser Gly Ile Asn Gly Asp Ile
    155             160                 165

CGG GCC AAG AGG ATT GCC AGC ATC ACG GAT GTG TGT GAG TCT         601
Arg Ala Lys Arg Ile Ala Ser Ile Thr Asp Val Cys Glu Ser
        170             175                 180

ATG AAG GAG CAG CTG CTG GTT CTG GTC GAA TGG GCC AAG TAC         643
Met Lys Glu Gln Leu Leu Val Leu Val Glu Trp Ala Lys Tyr
            185             190                 195
```

FIG.3B-1

```
ATC CCG GCC TTC TGT GAA CTT CTT CTG GAT GAC CAG GTG GCG    685
Ile Pro Ala Phe Cys Glu Leu Leu Leu Asp Asp Gln Val Ala
            200                     205

CTG CTC AGA GCC CAC GCT GGT GAG CAC CTG CTT CTG GGA GCC    727
Leu Leu Arg Ala His Ala Gly Glu His Leu Leu Leu Gly Ala
210                     215                     220

ACC AAG AGG TCC ATG GTG TTC AAG GAT GTG CTG CTC CTA GGC    769
Thr Lys Arg Ser Met Val Phe Lys Asp Val Leu Leu Leu Gly
        225                     230                 235

AAT GAC TAC ATC GTC CCT CGG CAC TGT CCA GAG CTA GCA GAG    811
Asn Asp Tyr Ile Val Pro Arg His Cys Pro Glu Leu Ala Glu
            240                     245             250

ATG AGC CGT GTG TCC ATT CGC ATC CTC GAT GAG CTG GTC TTG    853
Met Ser Arg Val Ser Ile Arg Ile Leu Asp Glu Leu Val Leu
                255                     260         265

CCC TTC CAA GAG CTG CAG ATC GAT GAT AAT GAA TAC GCC TGC    895
Pro Phe Gln Glu Leu Gln Ile Asp Asp Asn Glu Tyr Ala Cys
                    270                     275

CTC AAA GCC ATC ATC TTC TTT GAC CCA GAT GCC AAG GGG CTG    937
Leu Lys Ala Ile Ile Phe Phe Asp Pro Asp Ala Lys Gly Leu
280                     285                     290

AGT GAC CCA GGC AAG ATC AAG CGG CTG CGG TCA CAG GTG CAG    979
Ser Asp Pro Gly Lys Ile Lys Arg Leu Arg Ser Gln Val Gln
        295                     300                 305

GTG AGC CTG GAG GAT TAC ATC AAC GAC CGG CAG TAT GAC TCT   1021
Val Ser Leu Glu Asp Tyr Ile Asn Asp Arg Gln Tyr Asp Ser
            310                     315             320

CGG GGT CGT TTT GGA GAG CTG CTG CTC CTG CCC ACT CTG      1063
Arg Gly Arg Phe Gly Glu Leu Leu Leu Leu Leu Pro Thr Leu
                325                     330         335

CAG AGC ATT ACC TGG CAG ATG ATC GAG CAG ATC CAG TTC ATC   1105
Gln Ser Ile Thr Trp Gln Met Ile Glu Gln Ile Gln Phe Ile
                    340                     345

AAG CTC TTT GGC ATG GCC AAG ATT GAC AAC CTG CTG CAG GAG   1147
Lys Leu Phe Gly Met Ala Lys Ile Asp Asn Leu Leu Gln Glu
350                     355                     360

ATG CTG CTT GGA GGG TCT GCC AGT GAC GCG CCC CAC GCC CAC   1189
Met Leu Leu Gly Gly Ser Ala Ser Asp Ala Pro His Ala His
        365                     370                 375
```

FIG.3B-2

```
CAC CCC CTG CAC CCT CAC CTG ATG CAA GAA CAC ATG GGC ACC       1231
His Pro Leu His Pro His Leu Met Gln Glu His Met Gly Thr
            380             385                 390

AAT GTC ATA GTT GCC AAC ACG ATG CCC TCT CAC CTC ACG AAT       1273
Asn Val Ile Val Ala Asn Thr Met Pro Ser His Leu Thr Asn
            395             400                 405

GGA CAG ATG TCC ACC CCT GAG ACT CCA CAG CCA TCA CCA CCA       1315
Gly Gln Met Ser Thr Pro Glu Thr Pro Gln Pro Ser Pro Pro
                410             415

AGT GGC TCT GGA TCT GAA TCC TAC AAG CTC CTG CCA GGA GCC       1357
Ser Gly Ser Gly Ser Glu Ser Tyr Lys Leu Leu Pro Gly Ala
420             425                 430

ATC ACC ACC ATC GTC AAG CCT CCC TCT GCC ATC CCC CAG CCA       1399
Ile Thr Thr Ile Val Lys Pro Pro Ser Ala Ile Pro Gln Pro
        435             440                 445

ACG ATC ACC AAG CAG GAA GCC ATC TAG   CAAGCCGCCGGGGGGTGG      1444
Thr Ile Thr Lys Gln Glu Ala Ile AM
        450             455

GGGTGAGGCTTCTGCTGGCTCACACCCTCAGAGAGCGCCTGGGTGTAACTTAGTC       1499

ACGGCAAAGAGGATGTGACAAGAGGGACCAGTCCCAGAGCAGCCACTGAAAGGGC       1554

TTGTAGGCCCAAAAACATGCGCTGAGGATCGCATGCATTGCCACCCCTGACCCCA       1609

CATCCGGAGGGCAGGGCTTTGCCTTGAGGAGACCCCGGCGGGGGGATGTCTTCCG       1664

CTGCCTGGACTCTTCTCAAGTTGAAGCTGCCGTCTTCATCTTCCCCTCATATCTT       1719

CCCTCAACTTCTTCACCCCTAAAGGACAACCATCTGCAG                      1758

Translated Mol. Weight = 50579.43
```

FIG.3B-3

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1758 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: yes ( i v ) ANTI-SENSE: no (v) FRAGMENT TYPE: polymerase chain reaction product (vi) ORIGINAL SOURCE:
(A) ORGANISM: Rat liver nuclei (vii) IMMEDIATE SOURCE:
(B) CLONE: pf7

(ix) FEATURE:
(A) NAME/KEY: partial coding sequence for mature factor
(B) LOCATION:
(C) IDENTIFICATION METHOD: similarity to other members of the gene family
(D) OTHER INFORMATION: Translated Mol. Weight = 50579.43

(xi) SEQUENCE DESCRIPTION: SEQ ID NO:1:

```
CGACAGGGGG  CTGAGGGGTG  GGTAGAGGAG  AATGCGACTC  TCTAAAACCC  TCGCCGAC              58

ATG  GAC  ATG  GCT  GAC  TAC  AGT  GCT  GCC  TTG  GAC  CCA  GCC  TAC  ACC       103
Met  Asp  Met  Ala  Asp  Tyr  Ser  Ala  Ala  Leu  Asp  Pro  Ala  Tyr  Thr
 1              5                        10                       15

ACC  CTG  GAG  TTT  GAA  AAT  GTG  CAG  GTG  TTG  ACC  ATG  GGC  AAT  GAC       148
Thr  Leu  Glu  Phe  Glu  Asn  Val  Gln  Val  Leu  Thr  Met  Gly  Asn  Asp
                    20                       25                       30

ACA  TCC  CCA  TCT  GAA  GGT  GCC  AAC  CTC  AAC  TCA  TCC  AAC  AGC  CTG       193
Thr  Ser  Pro  Ser  Glu  Gly  Ala  Asn  Leu  Asn  Ser  Ser  Asn  Ser  Leu
                    35                       40                       45

GGT  GTC  AGT  GCC  CTG  TGT  GCC  ATC  TGT  GGC  GAT  CGG  GCC  ACT  GGC       238
Gly  Val  Ser  Ala  Leu  Cys  Ala  Ile  Cys  Gly  Asp  Arg  Ala  Thr  Gly
                    50                       55                       60

AAA  CAC  TAC  GGA  GCC  TCA  AGC  TGT  GAC  GGC  TGC  AAG  GGA  TTC  TTC       283
Lys  His  Tyr  Gly  Ala  Ser  Ser  Cys  Asp  Gly  Cys  Lys  Gly  Phe  Phe
                    65                       70                       75

AGG  AGG  AGC  GTG  AGG  AAG  AAC  CAC  ATG  TAC  TCC  TGC  AGG  TTT  AGC       328
Arg  Arg  Ser  Val  Arg  Lys  Asn  His  Met  Tyr  Ser  Cys  Arg  Phe  Ser
                    80                       85                       90

AGG  CAG  TGC  GTG  GTA  GAC  AAA  GAT  AAG  AGG  AAC  CAG  TGT  CGT  TAC       373
Arg  Gln  Cys  Val  Val  Asp  Lys  Asp  Lys  Arg  Asn  Gln  Cys  Arg  Tyr
                    95                      100                      105

TGC  AGG  CTC  AAG  AAG  TGC  TTC  CGG  GCT  GGC  ATG  AAG  AAA  GAA  GCC       418
Cys  Arg  Leu  Lys  Lys  Cys  Phe  Arg  Ala  Gly  Met  Lys  Lys  Glu  Ala
                   110                      115                      120

GTC  CAA  AAT  GAG  CGG  GAT  CGG  ATC  AGC  ACG  CGG  AGG  TCA  AGC  TAC       463
Val  Gln  Asn  Glu  Arg  Asp  Arg  Ile  Ser  Thr  Arg  Arg  Ser  Ser  Tyr
                   125                      130                      135

GAG  GAC  ATC  AGC  CTA  CCC  TCC  ATT  AAT  GCG  CTC  CTG  CAG  GCA  GAG       508
Glu  Asp  Ile  Ser  Leu  Pro  Ser  Ile  Asn  Ala  Leu  Leu  Gln  Ala  Glu
                   140                      145                      150

GTC  CTG  TCT  CAG  CAG  ATC  ACC  TCC  CCC  ATC  TCT  GGG  ATC  AAT  GGC       553
Val  Leu  Ser  Gln  Gln  Ile  Thr  Ser  Pro  Ile  Ser  Gly  Ile  Asn  Gly
                   155                      160                      165

GAC  ATT  CGG  GCC  AAG  AGG  ATT  GCC  AGC  ATC  ACG  GAT  GTG  TGT  GAG       598
Asp  Ile  Arg  Ala  Lys  Arg  Ile  Ala  Ser  Ile  Thr  Asp  Val  Cys  Glu
                   170                      175                      180

TCT  ATG  AAG  GAG  CAG  CTG  CTG  GTT  CTG  GTC  GAA  TGG  GCC  AAG  TAC       643
Ser  Met  Lys  Glu  Gln  Leu  Leu  Val  Leu  Val  Glu  Trp  Ala  Lys  Tyr
                   185                      190                      195

ATC  CCG  GCC  TTC  TGT  GAA  CTT  CTT  CTG  GAT  GAC  CAG  GTG  GCG  CTG       688
Ile  Pro  Ala  Phe  Cys  Glu  Leu  Leu  Leu  Asp  Asp  Gln  Val  Ala  Leu
                   200                      205                      210

CTC  AGA  GCC  CAC  GCT  GGT  GAG  CAC  CTG  CTT  CTG  GGA  GCC  ACC  AAG       733
Leu  Arg  Ala  His  Ala  Gly  Glu  His  Leu  Leu  Leu  Gly  Ala  Thr  Lys
```

```
                                   215                           220                              225
AGG  TCC  ATG  GTG  TTC  AAG  GAT  GTG  CTG  CTC  CTA  GGC  AAT  GAC  TAC        778
Arg  Ser  Met  Val  Phe  Lys  Asp  Val  Leu  Leu  Leu  Gly  Asn  Asp  Tyr
                    230                      235                      240

ATC  GTC  CCT  CGG  CAC  TGT  CCA  GAG  CTA  GCA  GAG  ATG  AGC  CGT  GTG        823
Ile  Val  Pro  Arg  His  Cys  Pro  Glu  Leu  Ala  Glu  Met  Ser  Arg  Val
                    245                      250                      255

TCC  ATT  CGC  ATC  CTC  GAT  GAG  CTG  GTC  TTG  CCC  TTC  CAA  GAG  CTG        868
Ser  Ile  Arg  Ile  Leu  Asp  Glu  Leu  Val  Leu  Pro  Phe  Gln  Glu  Leu
                    260                      265                      270

CAG  ATC  GAT  GAT  AAT  GAA  TAC  GCC  TGC  CTC  AAA  GCC  ATC  ATC  TTC        913
Gln  Ile  Asp  Asp  Asn  Glu  Tyr  Ala  Cys  Leu  Lys  Ala  Ile  Ile  Phe
                    275                      280                      285

TTT  GAC  CCA  GAT  GCC  AAG  GGG  CTG  AGT  GAC  CCA  GGC  AAG  ATC  AAG        958
Phe  Asp  Pro  Asp  Ala  Lys  Gly  Leu  Ser  Asp  Pro  Gly  Lys  Ile  Lys
                    290                      295                      300

CGG  CTG  CGG  TCA  CAG  GTG  CAG  GTG  AGC  CTG  GAG  GAT  TAC  ATC  AAC        1003
Arg  Leu  Arg  Ser  Gln  Val  Gln  Val  Ser  Leu  Glu  Asp  Tyr  Ile  Asn
                    305                      310                      315

GAC  CGG  CAG  TAT  GAC  TCT  CGG  GGT  CGT  TTT  GGA  GAG  CTG  CTG  CTG        1048
Asp  Arg  Gln  Tyr  Asp  Ser  Arg  Gly  Arg  Phe  Gly  Glu  Leu  Leu  Leu
                    320                      325                      330

CTC  CTG  CCC  ACT  CTG  CAG  AGC  ATT  ACC  TGG  CAG  ATG  ATC  GAG  CAG        1093
Leu  Leu  Pro  Thr  Leu  Gln  Ser  Ile  Thr  Trp  Gln  Met  Ile  Glu  Gln
                    335                      340                      345

ATC  CAG  TTC  ATC  AAG  CTC  TTT  GGC  ATG  GCC  AAG  ATT  GAC  AAC  CTG        1138
Ile  Gln  Phe  Ile  Lys  Leu  Phe  Gly  Met  Ala  Lys  Ile  Asp  Asn  Leu
                    350                      355                      360

CTG  CAG  GAG  ATG  CTG  CTT  GGA  GGG  TCT  GCC  AGT  GAC  GCG  CCC  CAC        1183
Leu  Gln  Glu  Met  Leu  Leu  Gly  Gly  Ser  Ala  Ser  Asp  Ala  Pro  His
                    365                      370                      375

GCC  CAC  CAC  CCC  CTG  CAC  CCT  CAC  CTG  ATG  CAA  GAA  CAC  ATG  GGC        1228
Ala  His  His  Pro  Leu  His  Pro  His  Leu  Met  Gln  Glu  His  Met  Gly
                    380                      385                      390

ACC  AAT  GTC  ATA  GTT  GCC  AAC  ACG  ATG  CCC  TCT  CAC  CTC  ACG  AAT        1273
Thr  Asn  Val  Ile  Val  Ala  Asn  Thr  Met  Pro  Ser  His  Leu  Thr  Asn
                    395                      400                      405

GGA  CAG  ATG  TCC  ACC  CCT  GAG  ACT  CCA  CAG  CCA  TCA  CCA  CCA  AGT        1318
Gly  Gln  Met  Ser  Thr  Pro  Glu  Thr  Pro  Gln  Pro  Ser  Pro  Pro  Ser
                    410                      415                      420

GGC  TCT  GGA  TCT  GAA  TCC  TAC  AAG  CTC  CTG  CCA  GGA  GCC  ATC  ACC        1363
Gly  Ser  Gly  Ser  Glu  Ser  Tyr  Lys  Leu  Leu  Pro  Gly  Ala  Ile  Thr
                    425                      430                      435

ACC  ATC  GTC  AAG  CCT  CCC  TCT  GCC  ATC  CCC  CAG  CCA  ACG  ATC  ACC        1408
Thr  Ile  Val  Lys  Pro  Pro  Ser  Ala  Ile  Pro  Gln  Pro  Thr  Ile  Thr
                    440                      445                      450

AAG  CAG  GAA  GCC  ATC  TAG  CAAGCCGCCG  GGGGTGGGG   GTGAGGCTTC                 1456
Lys  Gln  Glu  Ala  Ile
                    455

TGCTGGCTCA  CACCCTCAGA  GAGCGCCTGG  GTGTAACTTA  GTCACGGCAA  AGAGGATGTG  1516

ACAAGAGGGA  CCAGTCCCAG  AGCAGCCACT  GAAAGGGCTT  GTAGGCCCAA  AAACATGCGC  1576

TGAGGATCGC  ATGCATTGCC  ACCCCTGACC  CCACATCCGG  AGGGCAGGGC  TTTGCCTTGA  1636

GGAGACCCCG  GCGGGGGGAT  GTCTTCCGCT  GCCTGGACTC  TTCTCAAGTT  GAAGCTGCCG  1696

TCTTCATCTT  CCCCTCATAT  CTTCCCTCAA  CTTCTTCACC  CCTAAAGGAC  AACCATCTGC  1756

AG                                                                      1758
```

( 2 ) INFORMATION FOR SEQ ID NO:2:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: genomic DNA (iii) HYPOTHETICAL: yes (iv) ANTI-SENSE: no (v) FRAGMENT TYPE: polymerase chain reaction product (vi) ORIGINAL SOURCE:
  (A) ORGANISM: Rat liver nuclei (vii) IMMEDIATE SOURCE:
  (B) CLONE: cloned into polylinker region of Bluescript KS(+)

(ix) FEATURE:
  (A) NAME/KEY: primer for pep 1S
  (B) LOCATION: Near zinc finger
  (C) IDENTIFICATION METHOD: synthesized to pep 1
  (D) OTHER INFORMATION:

(xi) SEQUENCE DESCRIPTION: SEQ ID NO:2:

CCMTCCSANG GNGCNAAYYT NAA   23

(2) INFORMATION FOR SEQ ID NO:3:

(i) SEQUENCE CHARACTERISTICS:
  (A) LENGTH: 22 base pairs
  (B) TYPE: nucleic acid
  (C) STRANDEDNESS: single
  (D) TOPOLOGY: linear (ii) MOLECULE TYPE: genomic DNA (iii) HYPOTHETICAL: yes (iv) ANTI-SENSE: yes (v) FRAGMENT TYPE: polymerase chain reaction product (vi) ORIGINAL SOURCE:
  (A) ORGANISM: rat liver nuclei (vii) IMMEDIATE SOURCE:
  (B) CLONE: cloned into polylinker region of Bluescript KS(+)

(ix) FEATURE:
  (A) NAME/KEY: antisense of primer for pep 1A
  (B) LOCATION: near zinc finger
  (C) IDENTIFICATION METHOD: synthesized to pep 2
  (D) OTHER INFORMATION:

(xi) SEQUENCE DESCRIPTION: SEQ ID NO:3:

TTAGGTTNGC NCCYTSNSNN GG   22

(2) INFORMATION FOR SEQ ID NO:4:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (ii) MOLECULE TYPE: genomic DNA (iii) HYPOTHETICAL: yes ( i v ) ANTI-SENSE: no ( v ) FRAGMENT TYPE: polymerase chain reaction product ( v i ) ORIGINAL SOURCE:
    ( A ) ORGANISM: Rat liver nuclei ( v i i ) IMMEDIATE SOURCE:
    ( A ) CLONE: polylinker region of Bluescript KS(+)

( i x ) FEATURE:
    ( A ) NAME/KEY: primer 2S
    ( B ) LOCATION: entire sequence near zinc finger
        also at 20 and 29
    ( C ) IDENTIFICATION METHOD:
    ( D ) OTHER INFORMATION: N at locations 20 and 29 can be Y or A ( x i ) SEQUENCE DESCRIPTION: SEQ ID NO:4:

CATCTAGAAT TGAGCAGATN CARTTYATNA A                       31

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: yes ( i v ) ANTI-SENSE: yes ( v ) FRAGMENT TYPE: polymerase chain reaction product ( v i ) ORIGINAL SOURCE:
        ( A ) ORGANISM: Rat liver nuclei ( v i i ) IMMEDIATE SOURCE:
        ( A ) CLONE: polylinker region of Bluescript KS(+)

( i x ) FEATURE:
        ( A ) NAME/KEY: antisense to pep 2
        ( B ) LOCATION: entire sequence near zinc finger
            also at 14 and 23
        ( C ) IDENTIFICATION METHOD:
        ( D ) OTHER INFORMATION: N at locations 14 and 23 can be T or
            unknown ( x i ) SEQUENCE DESCRIPTION: SEQ ID NO:5:

AACGTCAGAG CTTNATRAAY TGNATYTGYT C                       31

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: yes ( i v ) ANTI-SENSE: no ( v ) FRAGMENT TYPE: polymerase chain reaction product ( v i ) ORIGINAL SOURCE:
        ( A ) ORGANISM: Rat liver nuclei ( v i i ) IMMEDIATE SOURCE:
        ( A ) CLONE: polylinker region of Bluescript KS(+)

( i x ) FEATURE:

(A) NAME/KEY: sense of pep 3
                (B) LOCATION: near zinc finger
                (C) IDENTIFICATION METHOD:
                (D) OTHER INFORMATION:

(x i) SEQUENCE DESCRIPTION: SEQ ID NO:6:

GAGGCTGTNC ANAAYGANMG NGA 23

(2) INFORMATION FOR SEQ ID NO:7:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (i i) MOLECULE TYPE: genomic DNA (i i i) HYPOTHETICAL: yes (i v) ANTI-SENSE: yes (v) FRAGMENT TYPE: polymerase chain reaction product (v i) ORIGINAL SOURCE:
                (A) ORGANISM: Rat liver nuclei (v i i) IMMEDIATE SOURCE:
                (A) CLONE: polylinker region of Bluescript KS(+)

(i x) FEATURE:
                (A) NAME/KEY: primer 3S
                (B) LOCATION: entire sequence near zinc finger
                        also at 3 and 5
                (C) IDENTIFICATION METHOD:
                (D) OTHER INFORMATION: N at location 3 may be C or G or T/U
                        N at location 5 may be G or T (x i) SEQUENCE DESCRIPTION: SEQ ID NO:7:

TCNCNCTCNT TYTGNACNGC YTC 23

(2) INFORMATION FOR SEQ ID NO:8:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (i i) MOLECULE TYPE: DNA (i v) ANTI-SENSE: NO (x i) SEQUENCE DESCRIPTION: SEQ ID NO:8:

GATCCTCGGG AAAGGGAAAC CGAAACTGAA GCC 33

LIVER ENRICHED TRANSCRIPTION FACTOR

TECHNICAL FIELD OF THE INVENTION

The present invention relates to liver-related transcription factors and, in particular, to such factors as participate in the regulation of a variety of genes such as certain of the apolipoproteins involved in fat and cholesterol transport.

This invention also relates to antibodies which recognize the receptor HNF-4, and antiidiotype antibodies that recognize both antibodies to HNF-4 and ligands which bind to HNF-4.

The invention also relates to antisense DNA and RNA molecules complementary to mRNA for HNF-4, and ribozymes which recognize the mRNA.

The invention also relates to methods of use of the aforementioned molecules, DNA sequences, antibodies, anti-idiotype antibodies, antisense molecules and ribozymes, for example in developing diagnostic and therapeutic agents to detect, inhibit or enhance binding to HNF-4.

It is a principal object of this invention to provide new means to study, diagnose, prevent and treat disease. More particularly, it is an object of this invention to provide molecules involved in binding to HNF-4, and to isolate other molecules which are themselves useful in inhibiting such binding.

This invention provides DNA sequences that code on expression for HNF-4, genomic DNA sequences for HNF-4, recombinant DNA molecules containing these DNA sequences, unicellular hosts transformed with these DNA molecules, processes for producing such receptors, and proteins essentially free of normally associated animal proteins.

The present invention also provides for antibody preparations reactive for HNF-4.

Monoclonal antibodies recognizing ligands to HNF-4 can inhibit ligand binding directly or by binding or otherwise interacting with a third molecule. Such molecules may act, for example, by changing the surface conformation of the ligand so that its affinity for the HNF-4 is reduced.

This invention also provides recombinant DNA molecules containing HNF-4 DNA sequences and unicellular hosts transformed with them. It also provides for HNF-4 proteins essentially free of normally associated animal proteins, methods for producing HNF-4, and monoclonal antibodies that recognize HNF-4.

This invention further provides methods for using antisense nucleic acids and ribozymes to inhibit HNF-4 expression. The invention also relates to methods for identifying binding inhibitors by screening molecules for their ability to inhibit binding of HNF-4 to its ligand. It provides methods for identifying ligands. One such method involves using anti-idiotypic antibodies against antibodies that recognize HNF-4 or HNF-4 ligands.

BACKGROUND OF THE INVENTION

Cell type specificity is based on differential gene expression which is in turn determined, at least in part, by the particular set of transcription factors present and active in a given cell at a given time. Many such factors have been identified and characterized, particularly in the liver where there is a wide range of transcriptionally controlled genes (McKnight & Palmiter, 1979; Derman et al., 1981). Some transcription factors, such as AP-1 and Sp-1, seem to be present in all cells at all times but other factors have a more limited distribution. Whether there is a discernible logic that explains the distribution of the many factors has yet to be determined. Two aspects of this problem are particularly important. The first aspect is to determine whether the distribution of factors in different issues is controlled at the level of transcription. If so, then a cascade of transcriptional regulation that ultimately results in cell specificity is indicated. The second issue is whether any particular factor is central to the accomplishment of a particular metabolic or physiologic goal. Such a goal might be suggested by factors acting on an interrelated set of genes.

These issues have begun to be addressed by the dissection and analysis of the promoter/enhancer regions of genes expressed primarily in hepatocytes by the present applicants and others (Johnson, 1990). The DNA elements that confer cell specific expression have been defined by transient transfection into Cultured cells (e.g., hepatoma vs. HeLa cells) and/or in vitro transcription assays, and the proteins that bind to these elements have been identified by DNA binding assays using crude liver nuclear extracts. In this way, at least four distinct protein factors that are abundant in liver have been found thus far: HNF1 (LF-B1) (Courtois et al., 1987; Monaci et al., 1988), C/EBP (Johnson et al., 1987), HNF-3 and HNF-4 (Costa et al., 1989). HNF1, a homeo domain protein (Frain et al., 1989; Baumhueter et al., 1990), C/EBP, the original leucine zipper protein (Landschulz et al., 1988), and most recently HNF-3A, a DNA binding protein that has no similarity to known transcription factor families (Lai et al., 1990) have all been purified and cloned so that distribution and regulation of each can be determined.

The following publications are cited in the body of the patent application. Each of the publications is incorporated herein by reference:

Ahe, von der D., Janich, S., Scheidereit, C., Renkawitz, R., Schutz, G., and Beato, M. (1985). Glucocorticoid and progesterone receptors bind to the same sites in two hormonally regulated promoters. *Nature*, 313, 706–709.

Baumhueter, S., Mendel, D. B., Conley, P. B., Kuo, C. J., Turk, C., Graves, M. K., Edwards, C. A., Courtois, G., and Crabtree, G. R. (1990). HNF-1 shares three sequence motifs with the POU domain proteins and is identical to LF-B1 and APF. *Genes and Development* 4, 372–379.

Beato, M. (1989). Gene regulation by steroid hormones. *Cell* 56, 335–344.

Birkenmeier, E. H., Gwynn, B., Howard, S., Jerry, J., Gordon, J. I., Landschulz, W. H., and McKnight, S. L. (1989). Tissue-specific expression, developmental regulation and mapping of the gene encoding CCAAT/enhancer binding protein. *Genes and Development*, 3, 1146–1156.

Brand, N., Petkovich, M., Krust, A., Chambon, P., de The, H., Marchio, A., Tiollais, P., and Dejean, A. (1988). Identification of a second human retinoic acid receptor. *Nature*, 332, 850–853.

Breslow, J. (1988). Apolipoprotein genetic variation and human disease. Physiol. Reviews, 68, 85–132.

Capon, D. J. et al. (1989). Designing CF4 immunoadhesins for AIDS therapy. *Nature*, 337, 525–531.

Carlsson, R., and Glad, C. (June, 1989). Monoclonal antibodies into the '90s. *Bio/Technology*, 7, 567–573.

Cate, R. et al. (1986). Isolation of the bovine and human genes for Mullerian inhibiting substance and expression of the human gene in animal cells. *Cell*, 45, 685–598.

Cech, T. R. (1988). Ribozymes and their medical implications. *J. Amer. Med. Assn.*, 260, 3030–3044.

Chomezynski, P. and Sacchi, N. (1987). Single-step method of RNA isolation by acid guanidinium thiocyanate-phenol-chloroform extraction. *Anal. Biochem.*, 162, 156–159.

Costa, R. H., Lai, E., and Darnell, J. E., Jr. (1986). Transcriptional control of the mouse prealbumin (transthyretin) gene: both promoter sequences and a distinct enhancer are cell specific. *Mol. and Cell. Biol.*, 6, 4697–4708.

Costa, R. H., Grayson, D. R., Xanthopoulos, K. G., and Darnell, J. E., Jr. (1988). A liver-specific DNA-binding protein recognizes multiple nucleotide sites in regulatory regions of transthyretin, a1-antitrypsin, albumin, and simian virus 40 genes. *Proc. Natl. Acad. Sci.*, 85, 3840–3844.

Costa, R. H., Grayson, D. R. and Darnell, J. E. Jr. (1989). Multiple hepatocyte-enriched nuclear factors function in the regulation of transthyretin and a1-antitrypsin genes. *Mol. and Cell. Biol.*, 9, 1415–1425.

Costa, R. H., Van Dyke, T. A., Yan, C., Kuo, F., and Darnell, J. E., Jr. (1990). Similarities in transthyretin gene expression and differences in transcription factors: liver and yolk sac compared to choroid plexus. *Proc. Natl. Acad. Sci. U.S.A.*, 87, 6589–6593.

Courtois, G., Morgan, J. G., Campbell, L. A., Fourel, G. and Crabtree, G. R. (1987). Interaction of a liver-specific nuclear factor with the fibrinogen and a1-antitrypsin promoters. *Science*, 238, 688–692.

Danielsen, M., Hinck, L., and Ringold, G. M. (1989). Two amino acids within the knuckle of the first zinc finger specify DNA response element activation by the glucocorticoid receptor. *Cell*, 57, 1131–1138.

Davis, M. M. (1986). Subtractive cDNA hybridization and the T-cell receptor gene. *Handbook of Experimental Immunology in Four Volumes*, 4th ed. Blackwell Scientific Publications, Oxford, England, 76.1–76.13.

Davis, M. M. et al. (1984). Cell type-specific cDNA probes and the murine I region: The localization and orientation of ad. *Proc. Natl. Acad. Sci. U.S.A.*, 81, 2194–2198.

Derman, E., Krauter, K., Walling, L., Weinberger, C., Ray, M. and Darnell, J. E. Jr. (1981). Transcriptional control in the production of liver-specific mRNAs. *Cell*, 23, 731–739.

de The, H., Marchio, A., Tiollais, P., and Dejean, A. (1987). A novel steroid thyroid hormone receptor-related gene inappropriately expressed in human hepatocellular carcinoma. *Nature*, 330, 667–670.

Duguid, J. R. et al. (1988). Isolation of cDNAs of scrapie-modulated RNMAs by subtractive hybridization of a cDNA library. *Proc. Natl. Acad. Sci. U.S.A.*, 85, 5738–5742.

Evans, R. M. (1988). The steroid and thyroid hormone receptor superfamily. *Science*, 240, 889–895.

Fawell, S. E., Lees, J. A., White, R. and Parker, M. G. (1990). Characterization and colocalization of steroid binding and dimerization activities in the mouse estrogen receptor. *Cell*, 60, 953–962.

Feinberg, A. P., and Vogelstein, B. (1983). A technique for radiolabeling DNA restriction endonuclease fragments to high specific activity. *Anal. Biochem.*, 132, 6–13.

Fisher, R. A. et al. (1988). HIV infection is blocked in vitro by recombinant soluble CD4. *Nature*, 331, 76–78.

Forman, B. M., Yan, C. R., Au, M., Casanova, J., Ghysdael, J., and Samuels, H. H. (1989). A domain containing leucine-zipper-like motifs mediate novel in vivo interactions between the thyroid hormone and retinoic acid receptors. *Mol. End.*, 3, 1610–1626.

Forman, B. M. and Samuels, H. H. (1990). Interactions among a subfamily of nuclear hormone receptors: The regulatory zipper model. *Mol. End.* 4, 1293–1301.

Frain, M., Swart, G., Monaci, P., Nicosia, A., Stampfli, S., Frank, R., and Cortese, R. (1989). The liver-specific transcription factor LF-B1 contains a highly diverged homeobox DNA binding domain. *Cell*, 59, 145–157.

Fried, M. and Crothers, D. M. (1981). Equilibria and kinetics of lac repressor-operator interactions by polyacrylamide gel electrophoresis. *Nucleic Acids Res.*, 9, 6505–6525.

Giguere, V., Yang, N., Segui, P., and Evans, R. M. (1988). Identification of a new class of steroid hormone receptors. *Nature*, 331, 91–94.

Glass, C. K., Lipkin, S. M., Devary, O. V., and Rosenfeld, M. G. (1989). Positive and negative regulation of gene transcription by a retinoic acid-thyroid hormone receptor heterodimer. *Cell*, 59, 697–708.

Gorman, C. M., Moffat, L. F. and Howard, B. H. (1982). Recombinant genomes which express chloramphenicol acetyltransferase in mammalian cells. *Mol. Cell. Biol.*, 2, 1044–1051.

Gorman, C. M., Howard, B. H. and Reeves, R. (1983). Expression of recombinant plasmids in mammalian cells is enhanced by sodium butyrate. *Nucleic Acids Res.*, 11, 7631–7648.

Gorski, K., Carneiro, M. and Schibler, U. (1986). Tissue-specific in vitro transcription from the mouse albumin promoter. *Cell*, 47, 767–776.

Green, N., Alexander, H., Olson, A., Alexander, S., Shinnick, T. M., Sutcliffe, J. G., and Lerner, R. A. (1982). Immunogenic structure of the influenza virus hemagglutinin. *Cell*, 28, 477–487.

Green, S., Walter, P., Kumar, V., Krust, A., Bornert, J. M., Argos, P., and Chambon, P. (1986). Human oestrogen receptor cDNA: Sequence, expression and homology to c/epb. *Nature*, 320, 134–139.

Green, S. and Chambon, P. (1988). Nuclear receptors enhance our understanding of transcription regulation. *Trends Genet.*, 4, 309–314.

Gubler, U., and Hoffman, B. J. (1983). A simple and very efficient method for generating cDNA libraries. *Gene*, 25, 263–269.

Hamada, K., Gleason, S. L., Levi, B. Z., Hirschfeld, S., Appella, E., and Ozato, K. (1989). H-2RIIBP, a member of the nuclear hormone receptor superfamily that binds to both the regulatory element of major histocompatibility class I genes and the estrogen response element. *Proc. Natl. Acad. Sci. U.S.A.*, 86, 8289–8293.

Hambor, J. E. et al. (1988). Functional consequences of antisense RNA-mediate inhibition of CD8 surface expression in a human T cell clone. *J. Exp. Med.*, 168, 1237–1245.

Hardon, E. M., Frain, M., Paonessa, G. and Cortese, R. (1988). Two distinct factors interact with the promoter regions of several liver-specific genes. *The EMBO J.*, 7, 1711–1719.

Harlow, E. and Lane, D. (1988). *Antibodies: A laboratory manual.* (Cold Spring Harbor, N.Y.: Cold Spring Harbor Lab.)

Hasselhoff, J., and Gerlach, W. L. (1988). Simple RNA enzymes with new and highly specific endoribonuclease activities. *Nature*, 334, 585–591.

Hedrick, S. M. et al. (1984). Isolation of cDNA clones encoding T cell-specific membrane-associated proteins. *Nature*, 308, 149–153.

Ito, Y., Azrolan, N., O'Connell, A., Walsh, A., and Breslow, J. L. (1990) Hypertriglyceridemia as a result of human apoCIII gene expression in transgenic mice. *Science*, 249, 790–793.

Johnson, P. F., Landschulz, W. H., Graves, B. J., and McKnight, S. L. (1987). Identification of a rat liver nuclear protein that binds to the enhancer core element of three animal viruses. *Genes and Development*, 1, 133–146.

Johnson, P. F. (1990). Transcriptional activators in hepatocytes. In *Cell Growth and Differentiation*, 1, 47–52.

Kadonaga, J. T., and Tjian, R. (1986). Affinity purification of sequence-specific DNA binding proteins. *Proc. Natl. Acad. Sci. U.S.A.*, 83, 5889–5893.

Kennedy, R. C. et al. (July, 1986). Anti-idiotypes and immunity. *Sci. Am.*, 255, 48–56.

Kozak, M. (1987). An analysis of 5'-noncoding sequences from 699 vertebrate messenger RNA's. *Nucleic Acids Res.*, 15, 8125–8143.

Krebs, E., Eisenman, R., Kuenzel, E., Litchfield, D., Lozeman, F., Lischer, B. and Sommercom, J. (1988). Casein kinase II as a potentially important enzyme concerned with signal transduction. In *Molecular Biology of Signal Transduction*. (Cold Spring Harbor, N.Y.: Cold Spring Harbor Laboratory), p. 77–84.

Kumar, V., and Chambon, P. (1988). The estrogen receptor binds tightly to its responsive element as a ligand-induced homodimer. *Cell*, 55: 145–156.

Kuo, C. F., Xanthopoulos, K. G., and Darnell, J. E. Jr. (1990). Fetal and adult localization of C/EBP: evidence for combinatorial action of transcription factors in cell-specific gene expression. *Development*, 109, 473–481.

Lai, E., Prezioso, V. R., Smith, E., Litvin, O., Costa, R. H., and Darnell, J. E., Jr. (1990). HNF-3A, a hepatocyte-enriched transcription factor of novel structure is regulated transcriptionally. *Genes and Development*, 4, 1427–1436.

Landschulz, W. H., Johnson, P. F., Adashi, E. Y., Graves., B. J., and McKnight, S. L. (1988). Isolation of a recombinant copy of the gene encoding C/EBP. *Genes and Development*, 2, 786–800.

Lathe, E. (1985). Synthetic oligonucleotide probes deduced from amino acid sequence data: Theoretical and practical considerations. *J. Mol. Biol.*, 183, 1–12.

Leff, T., Reue, K., Melian, A., Culver, H., and Breslow, J. L. (1989). A regulatory element in the ApoCIII promoter that directs hepatic specific transcription binds to proteins in expressing and nonexpressing cell types. *The J. of Biol. Chem.*, 264, 16132–16137.

Lew, D. J., Decker, T., Strehlow, I. and Darnell, J. E. (1990). Overlapping elements in the GBP gene promoter mediate transcriptional induction by alpha and gamma-interferon. *Mol. Cell Biol.*, in press.

Li, Y., Shen, R.-F., Tsai, S. Y., and Woo, S. L. C. (1988). Multiple hepatic trans-acting factors are required for in vitro transcription of the human alpha-1-antitrypsin gene. *Mol. and Cell. Biol.*, 8, 4362–4369.

MacGregor, G. R., and Caskey, C. T. (1989). Construction of plasmids that express *E. coli* b-galactosidase in mammalian cells. *Nucleic Acids Res.*, 17, 2365.

Mader, S., Kumar, V., de Verneuil, H., and Chambon, P. (1989). Three amino acids of the oestrogen receptor are essential to its ability to distinguish an oestrogen from a glucocorticoid-responsive element. *Nature*, 338, 271–274.

Mangelsdorf, D. J., Ong, E. S., Dyck, J. A. and Evans, R. M. (1990). Nuclear receptor that identifies a novel retinoic acid response pathway. *Nature*, 345, 224–229.

Maniatis, T., Fritsch, E. F., and Sambrook, J. (1982). *Molecular cloning: A laboratory manual.* (Cold Spring Harbor, N.Y.: Cold Spring Harbor Lab.)

Marcus-Sekura, C. J. (1988). Techniques for using antisense oligonucleotides to study gene expression. *Anal. Biochem.*, 172, 289–295.

Matsudaira, P. (1987). Sequence from picomole quantities of proteins electroblotted onto polyvinylidene difluorid membranes. *The J. of Biol. Chem.*, 262, 10035–10038.

McKnight, G. S., and Palmiter, R. D. (1979). Transcriptional regulation of the ovalbumin and conalbumin genes by steroid hormones in chick oviduct. *J. Biol. Chem.*, 254, 9050–9058.

Mermod, N., O'Neill, E. A., Kelly, T. J. and Tjian, R. (1989). The proline-rich transcriptional activator of CTF/NF-1 is distinct from the replication and DNA binding domain. *Cell*, 58, 741–753.

Miyajiima, N., Kadowaki, Y., Fukushige, Shiminizu, S., Semba, K., Yamanashi, Y. H., Matsubara, K., Toyoshima, K., and Yamanoto, T. (1988). Identification of two novel members of erbA superfamily by molecular cloning: The gene products of the two are highly related to each other. *Nucleic Acids Res.*, 16:11057–11074.

Monaci, P., Nicosia, A., and Cortese, R. (1988). Two different liver-specific factors stimulate in vitro transcription from the human a1-antitrypsin promoter. *The EMBO J.*, 7, 2075–2087.

Mueller, C. R., Maire, P., and Schibler, U. (1990). DBP, a liver-enriched transcriptional activator, is expressed late in ontogeny and its tissue specificity is determined posttranscriptionally. *Cell*, 61, 279–291.

Pearson, W. R., and Lipman, D. J. (1988). Improved tools for biological sequence comparison. *Proc. Natl. Acad. Sci. U.S.A.*, 85, 2444–2448.

Puissant, C., and Houdebine, L. M. (1990). An improvement of the single-step method of RNA isolation by acid guanidinium thiocyanate-phenol-chloroform extraction. *BioTechniques*, 8, 148–149.

Reue, K., Leff, T., and Breslow, J. L. (1988). Human apolipoprotein CIII gene expression is regulated by positive and negative Cis-acting elements and tissue-specific protein factors. *The J. of Biol. Chem.*, 263, 6857–6864.

Rosen, C. A., Sodroski, J. G. and Haseltine, W. A. (1985). The location of cis-acting regulatory sequences in the human T cell lymphotropic virus type III (HTLV-III/LAV) long terminal repeat. *Cell*, 41, 813–823.

Ruppert, S., Boshart, M., Bosch, F. X., Schmid, W., Fournier, R. E. K., and Schutz, G. (1990). Two genetically defined trans-acting loci coordinately regulate overlapping sets of liver-specific genes. *Cell*, 61, 895–904.

Ryseck, R. P., Macdonald-Bravo, H., Mattei, M. G., Ruppert, S., and Bravo, R. (1989). Structure, mapping and expression of a growth factor inducible gene encoding a putative nuclear hormonal binding receptor. *The EMBO J.*, 8, 3327–3335.

Saiki, R. K., Gelfand, D. H., Stoffel, S., Scharf, S. J., Higuchi, R., Horn, G. T., Mullis, K. B., and Erlich, H. A. (1988). Primer-directed enzymatic amplification of DNA with a thermostable DNA polymerase. *Science*, 239, 487–491.

Sanger, F., Nicklen, S., and Coulson, A. R. (1977). DNA sequencing with chain terminating inhibitors. *Proc. Natl. Acad. Sci. U.S.A.*, 74, 5463–5467.

Sambrook, J., Fritsch, E. F., and Maniatis, T. (1989). *Molecular Cloning: A laboratory manual.* (Cold Spring Harbor, N.Y.: Cold Spring Harbor Laboratory).

Sargent, T. D. (1987). Isolation of differentially expressed genes. *Methods in Enzymol.*, 152, 423–447.

Schule, R., Umesono, K., Mangelsdorf, D. J., Bolado, J., Pike, J. W., and Evans, R. M. (1990). Jun-fos and receptors for vitamins A and D recognize a common response element in the human osteocalcin gene. *Cell*, 61, 497–504.

Seed, B. (1987). An LFA-3 cDNA encodes a phospholipid-linked membrane protein homologous to its receptor CD2. *Nature*, 329, 840–842.

Seed, B., and Aruffo, A. (1987). Molecular cloning of the CD2 antigen, the T-cell erythrocyte receptor, by a rapid immunoselection procedure. *Proc., Natl. Acad. Sci, U.S.A.*, 84, 3365–3369.

Tsai, S. Y., Carlstedt-Duke, J., Weigel, N. L., Dahlman, K., Gustafsson, J. A., Tsai, M. J., and O'Malley, B. W. (1988). Molecular interactions of steroid hormone receptor with its enhancer element: Evidence for receptor dimer formation. *Cell*, 55, 361–369.

Umesono, K., Giguere, V., Glass, C. K., Rosenfeld, M. G., and Evans, R. M. (1988). Retinoic acid and thyroid hormone induce gene expression through a common responsive element. *Nature*, 336, 262–265.

Umesono, K. and Evans, R. M. (1989). Determinants of target gene specificity for steroid/thyroid hormone receptors. *Cell*, 57, 1139–1146.

Vaulont, S., Puzenat, N., Kahn, A., and Raymondjean, M. (1989). Analysis by cell-free transcription of the liver-specific pyruvate kinase gene promoter. *Mol. and Cell. Biol.*, 9, 4409–4415.

Wang, L. H., Tsai, S. Y., Cook, R. G., Beattie, W. G., Tsai, M. J. and O'Malley, B. W. (1989). COUP transcription factor is a member of the steroid receptor superfamily. *Nature*, 340, 163–166.

Weinberger, C., Thompson, C. C., Ong, E. S., Lebo, R., Gruo, D. J., and Evans, R. M. (1986). The c/epb gene encodes a thyroid hormone receptor. *Nature*, 234, 641–646.

Wingender, E. (1990). Transcription regulating proteins and their recognition sequences. *Critical Reviews in Eukaryotic Gene Expression*, 1, 11–48.

Wysocki, L. J., and Sato, V. L. (1978). Panning for lymphocytes: A method for cell selection. *Proc. Natl. Acad. Sci. U.S.A.*, 75, 2844–2848.

Xanthopoulos, K. G., Mirkovitch, J., Decker, T., Kuo, C. F., and Darnell, J. E., Jr. (1989). Cell-specific transcriptional control of the mouse DNA-binding protein mC/EBP. *Proc. Natl. Acad. Sci. U.S.A.* 86, 4117–4121.

Yamasaki, K. et al. (1988). Cloning and expression of the human interleukin-6 (BSF-2/IFNB2) receptor. *Science*, 241, 825–828.

Young, R. A. and Davis, R. W. (1983). Efficient isolation of genes by using antibody probes. *Proc. Natl. Acad. Sci. U.S.A.*, 80, 1194–1198.

SUMMARY OF THE INVENTION

The present invention comprises the purification and cloning of HNF-4 (hepatocyte nuclear factor 4), a factor originally detected in crude liver extracts as binding to a DNA element required for the transcription of the transsthyretin (TTR) gene in hepatoma cells (Costa et al., 1989). An amino acid sequence comparison indicates that HNF-4 is a member of the superfamily of steroid/thyroid hormone receptors, ligand-dependent transcription factors which are known to play a role in differentiation and development (Evans, 1988; Gereen & Chambon, 1988; /Beato, 1989). Whereas all of the other members to date fall into one of several subfamilies based on the nucleotide sequence of their recognition sites and the amino acid sequence of the zinc finger region (Umesono & Evans, 1989; Forman & Samuels, 1990), HNF-4 appears to represent a new subfamily.

More particularly, the present transcription factor is believed to play a regulatory role in the formation of lipid carrying proteins such as Apo CIII, as well as possible effects on Apo A1, Apo B, pyruvate kinase, α1 antitrypsin and glutamine synthetase. The cDNA sequence has been identified, and the invention relates to the DNA sequence, recombinant molecules based thereon, probes, sense and antisense RNA, and appropriately transformed host cells. Diagnostic and therapeutic applications are likewise contemplated.

(A) SDS-PAGE Analysis of HNF-4 Purification from Rat Liver Nuclei. Equivalent fractions of the starting material for each of the five last chromatographic steps and the peak fraction from the Mono Q column (Fxn 38) are shown in a Coomassie blue-stained gel. Oligo #1 and #2 are DNA affinity columns made from HNF-4P and APF-1 oligonucleotides, respectively. The band in Fxn 38 was estimated to be 54 kD based on the relative mobility of the Markers: 97, 66, 43 and 31 kD, top to bottom.

(B) Characterization of the Binding Activity of Purified HNF-4 Protein. The protein-DNA complexes from a mobility-shift assay (0.0625 μl Mono Q Fxn 38, 3 μg BSA, 0.5 μg poly(dl-dC) with seven $^{32}$P-labeled oligonucleotide probes (1 ng) with and without 50-fold excess competitor are shown. APF1, −151=−151 to −130, 4P=HNF4P, 4D=HNF4D as in Table 1. Nonspecific probes are from the mouse TTR promoter: −175=−175 to −151 (Costa et al., 1986), HNF3 (−111 to −85, Costa et al., 1989) and c/EBP (−186 kb, site 3, Costa et al., 1988).

(C) Renaturation of HNF-4 Protein. Fifty nanograms of Mono Q-purified HNF-4 was fractionated by SDS-PAGE and the protein eluted from a series of gel slices was tested for binding to the APF1 probe (0.5 ng) in a mobility-shift assay. Competitor was 50-fold excess unlabeled APF1 oligonucleotide. The protein gel lane shown was run in parallel to the dissected lane and is silver stained.

FIG. 2—Characterization of Purified HNF-4

(A) Footprint: Purified HNF-4 (Fxn 38) was used to footprint both strands of the −202 to −70 region of the mouse TTR promoter with copper phenanthroline. "F" and "B" are free and bound probe. "G" designates probe cleaved at G residues. The footprinted regions are shown in brackets; the arrow points to a hypersensitive site.

(B) Phosphatase and Protease Studies: Purified HNF-4 (Fxn 38) was incubated at 37° C. (−) in the presence of calf intestine alkaline phosphatase (CIP), Protease V8 (V8), or Endoproteinase Lys C (lysC). The treated material was divided into four aliquots and tested in the mobility-shift assay with the designated probes.

Figure 3A:
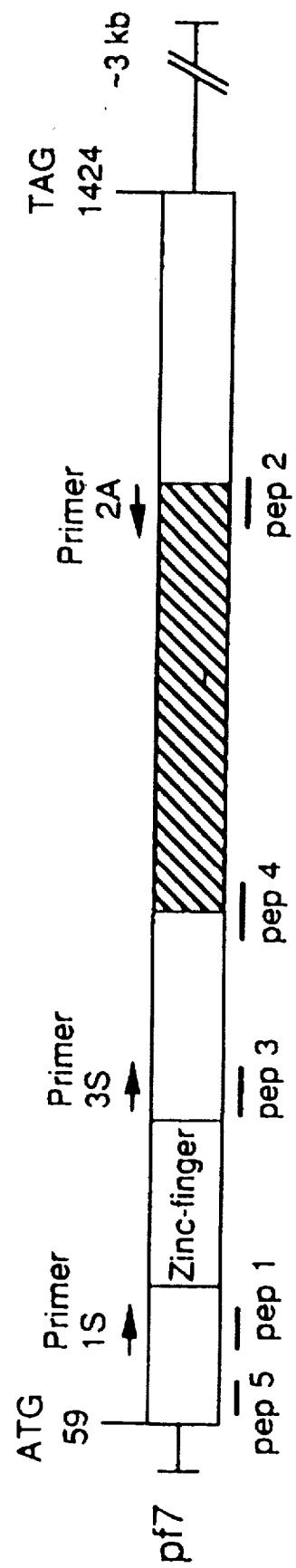

FIG. 3—Nucleotide Sequence of HNF-4 cDNA and Deduced Amino Acid Sequence of HNF-4 Protein (A) Schematic Representation of the Largest HNF-4 Clone, pf7. The positions of the peptides obtained from CNBr-cleavage of the purified protein (pep 1–5,-plain lines) and the corresponding oligonucleotide primers which yielded products in PCR (arrows) (not drawn to scale) are shown. The open reading frame starting from the second in-frame methionine (see text) is delineated by the box. Numbers are the nucleotide positions from the beginning of the cDNA. The hatched area denotes the region used to probe a rat liver cDNA library for a full length clone. "Zinc finger" refers to the section of similarity to the steroid hormone receptors.

(B) Partial Nucleotide Sequence and Deduced Amino Acid Sequence of HNF-4 cDNA. Sequence was obtained from the PCR products, pf7 and other cDNA isolates by the dideoxy method (Sanger et al., 1977). All regions were sequenced from at least two sources and were verified in the pf7 clone. The underlined amino acid sequences correspond to peptides 1.5. "+1" marks the probable initiator methionine. The bracket marks the knuckle of the first zinc finger and the (*) denotes the novel asp residue (see text). The sequence has been submitted to GenBank.

Figure 4:
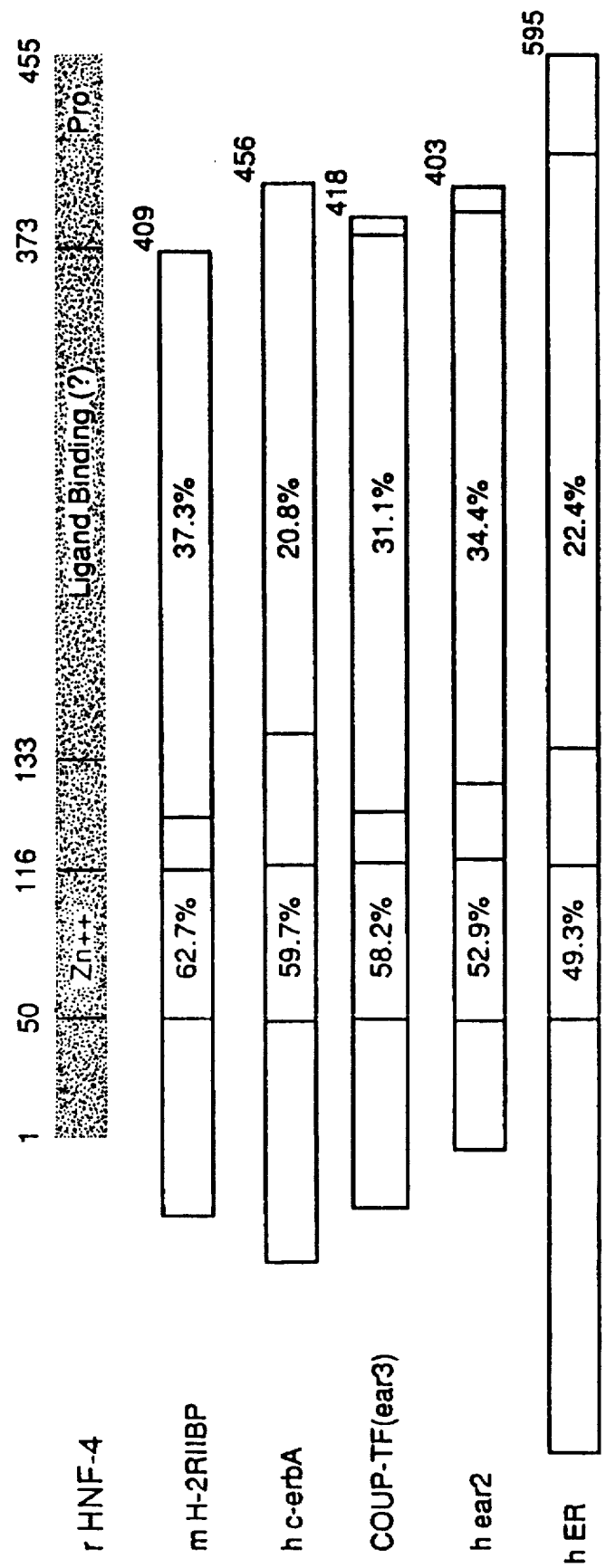

FIG. 4—Structural and Sequence Similarity Between HNF-4 Protein and steroid Hormone Receptors The primary amino acid sequences of rat HNF-4 was compared to members of the receptor superfamily using the FASTA program (Pearson & Lipman, 1988). Percentages denote amino acid identity within the zinc finger (Zn++) and ligand binding domains. "Pro" refers to a proline-rich domain. mH2-RIIBP is a mouse major histocompatibility class I regulatory protein (Hamada et al., 1989); h c-erbA is the human thyroid hormone receptor $T_3R_\beta$ (Weinberger et al., 1986 ); h ER is the human estrogen receptor (Green et al., 1986); COUP-TT(ear3) is the chicken ovalbumin upstream promoter transcription factor (Wang et al., 1989) and h ear 2 is a human v-erbA-related gene (Miyajima et al., 1988).

FIG. 5—In vitro Synthesized HNF-4 Protein Binds to Its Recognition Site as a Dimer (A) Schematic Representation of Truncated Forms of HNF-4 Protein Synthesized in Vitro. pf7 DNA (in Bluescript SK(−)) was cut with the restriction enzymes indicated and transcribed in vitro with T3 RNA polymerase. The resulting mRNAs were translated with rabbit reticulate lysate (Promega) in the presence of $^3$H-leucine. The open box represents the 3 kb cDNA insert in pf7; the numbers are the nucleotide position of the start (ATG) and stop (TAG). The position of the cut site of the restriction enzymes and the length of the polypeptide in amino acids (aa) resulting from translation beginning at nucleotide 59 are given.

(B) Mobility-Shift Assay of in vitro Synthesized HNF-4 Products. Reactions contained 0.5 ng $^{32}$P-labeled APF1 probe and 2 µg poly(dl-dC) in the presence of 25 ng unlabeled nonspecific (−) (−175 to −151 TTR) or specific (+) oligonucleotide (APF1) as competitor. Lanes 1–2: purified HNF-4 (Fxn 38); lanes 3–12: in vitro translation reactions (2 µ) as described in (A); lanes 13–14: Bovine Mosaid Virus (BMV) RNA added to the in vitro translation system as a negative control.

(C) SDS-PAGE of in vitro Synthesized HNF-4 Products. Autoradiogram of a 10% gel (treated with Enhance, NEN) containing 1 µl of translation reactions described in (A). The positions of Coomassie-stained markers are shown on the left.

(D) Mobility-Shift Assay Showing Dimer Formation. pf7 DNA cut with the restriction enzymes indicated was transcribed as in (A). The resulting RNAs were mixed as noted and translated in vitro. The translation reactions were assayed as in (B) in the presence of nonspecific competitor. The arrows indicate the complexes formed by heterodimeric protein; the arrow head marks the shift complex normally seen, presumably a homodimer.

Figure 6A:
Figure 6B:
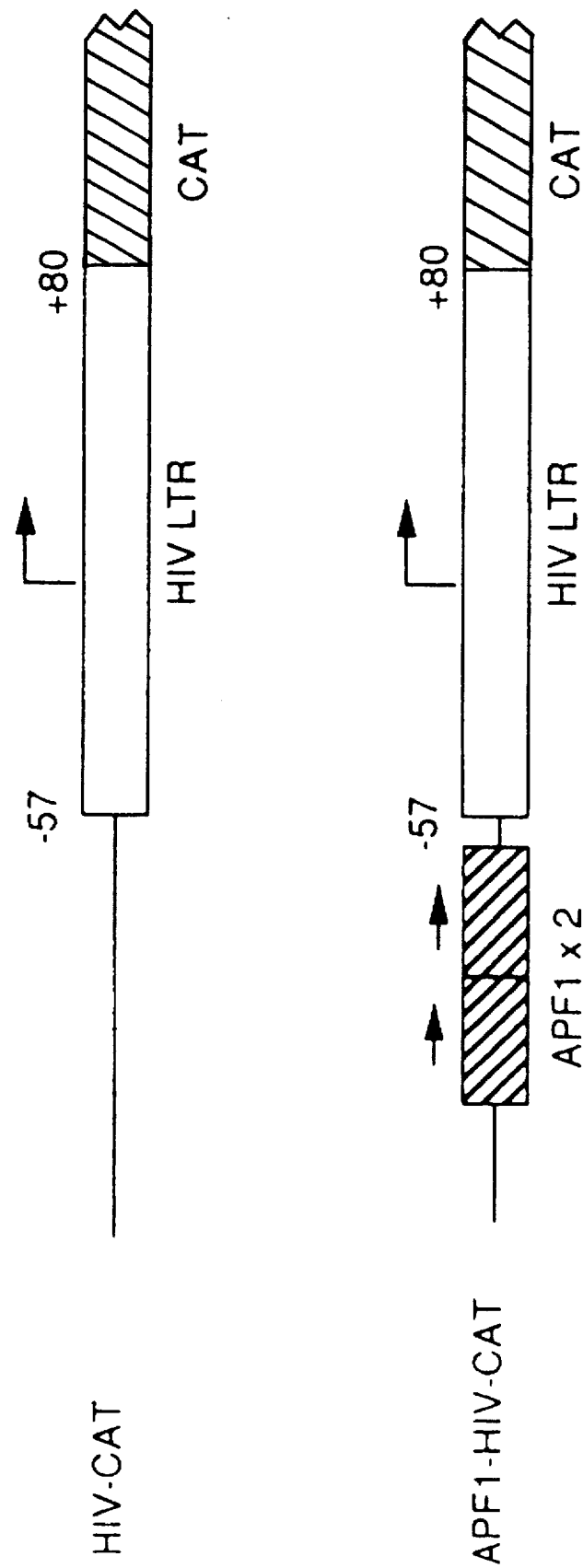

FIG. 6—Transcriptional Activation by HNF-4 cDNA

Top: autoradiogram of CAT assay. Bottom: schematic representation of reporter constructs. Expression vector DNA (0–5.0 µg) containing HNF-4 cDNA (the 3 kb insert of pf7) in either the sense or antisense direction was cotransfected into HeLa cells with a CAT reporter construct (2 µg), either lacking (HIV-CAT) or containing HNF-4 recognition sites (APF1-HIV-CAT). The long terminal repeat (LTR) of the human immunodeficiency virus (HIV) served as the basal promoter element. Densitometry of the autoradiogram indicated a 10–15 fold induction by HNF-4 cDNA (lane 2–4 compared to lanes 9–11).

Figure 7:
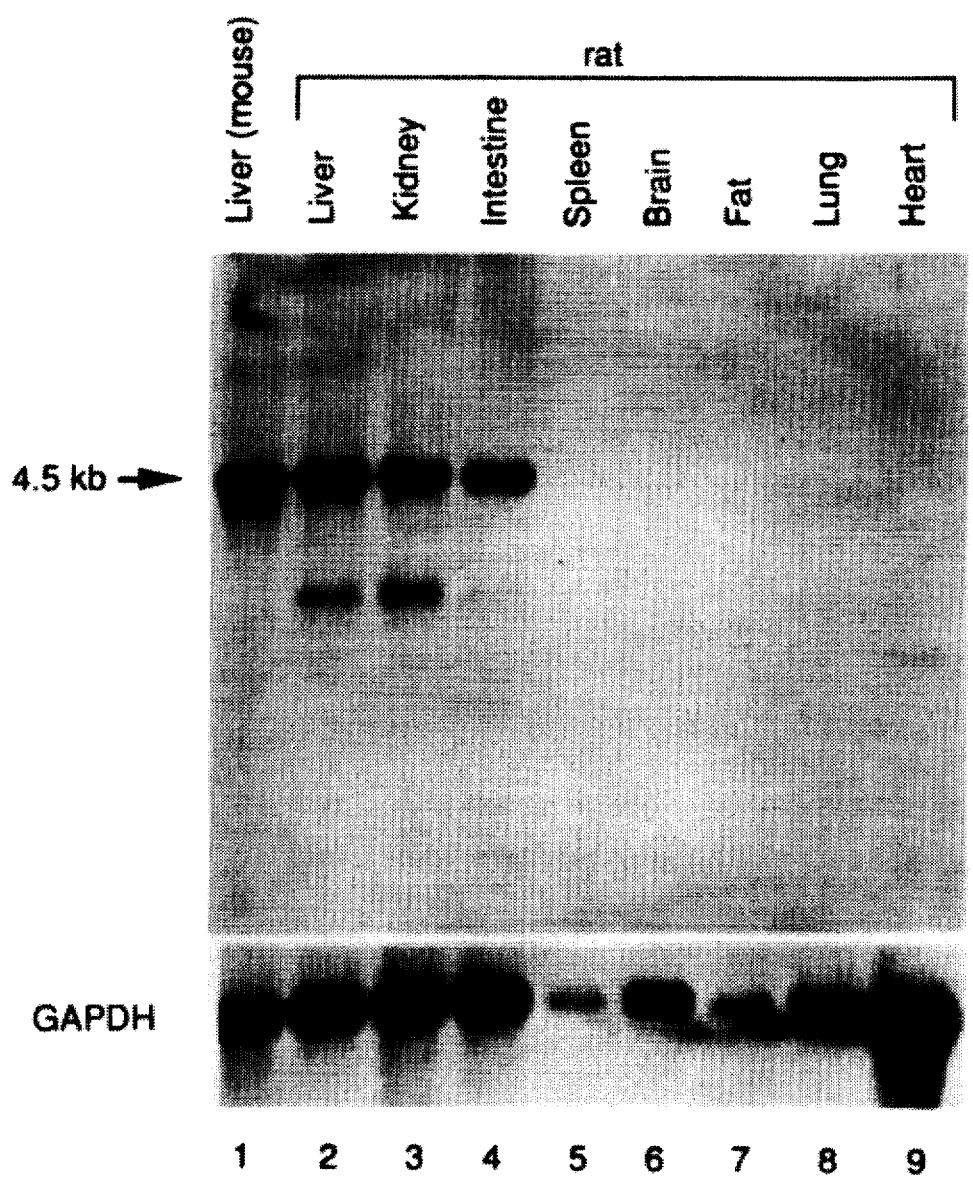

FIG. 7—Limited Tissue Distribution of HNF-4 mRNA

Northern blot analysis of poly(A)+ RNA from different rat and mouse tissues using an HNF-4 cDNA fragment as probe (top). A glyceraldehyde 3-phosphate dehydrogenase (GAPDH) probe served as a control (bottom).

Figure 8:
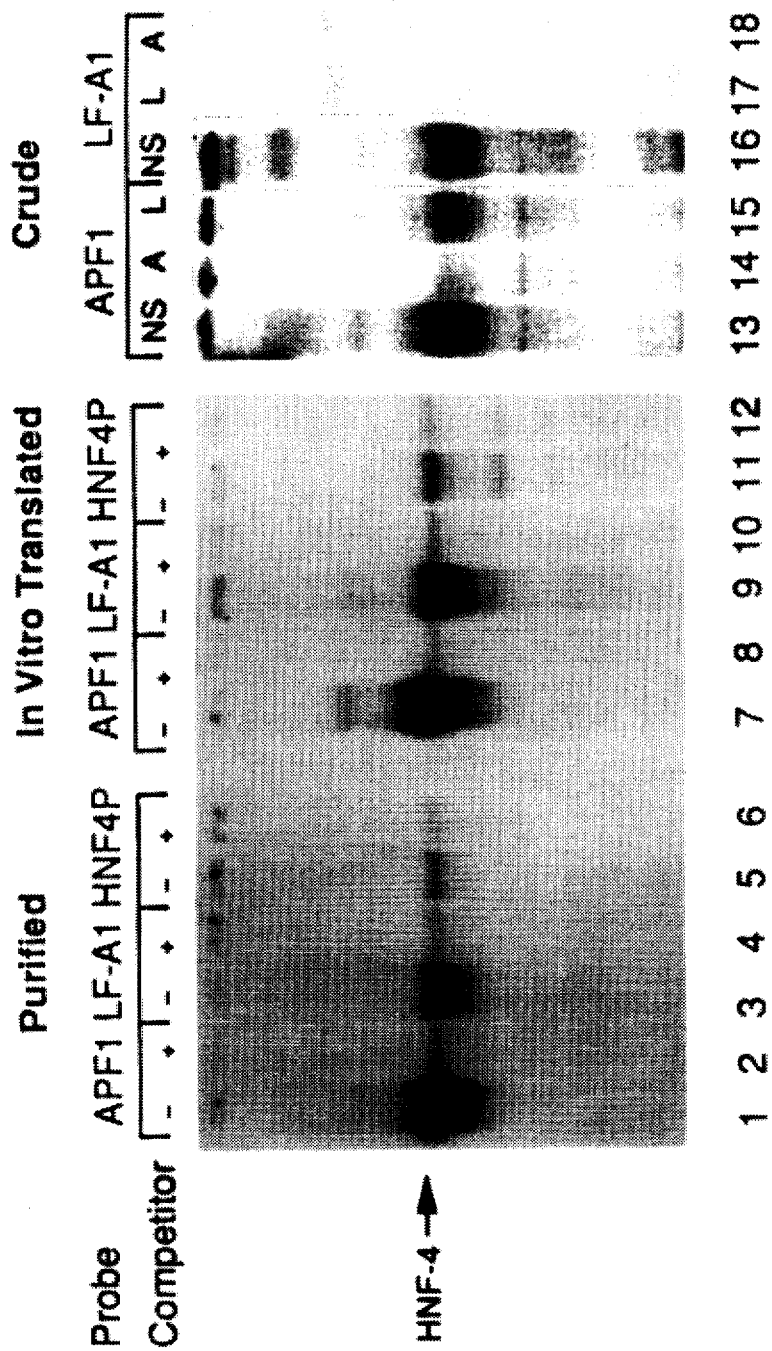

FIG. 8—HNF-4 Binds to an LF-A1 Site (A) Mobility-shift assay with either purified (MonoQ, Fxn 38, 0.03 µl) or in vitro translated HNF-F (Sph 1, FIG. 5, 2 µg poly(dl-dC) and 25 ng of unlabeled oligonucleotide, either nonspecific (−) (−175 to −151 TTR) or specific (+) oligonucleotide (APF1, LF-A1 or HNF4P) as competitor.

Figure 9:
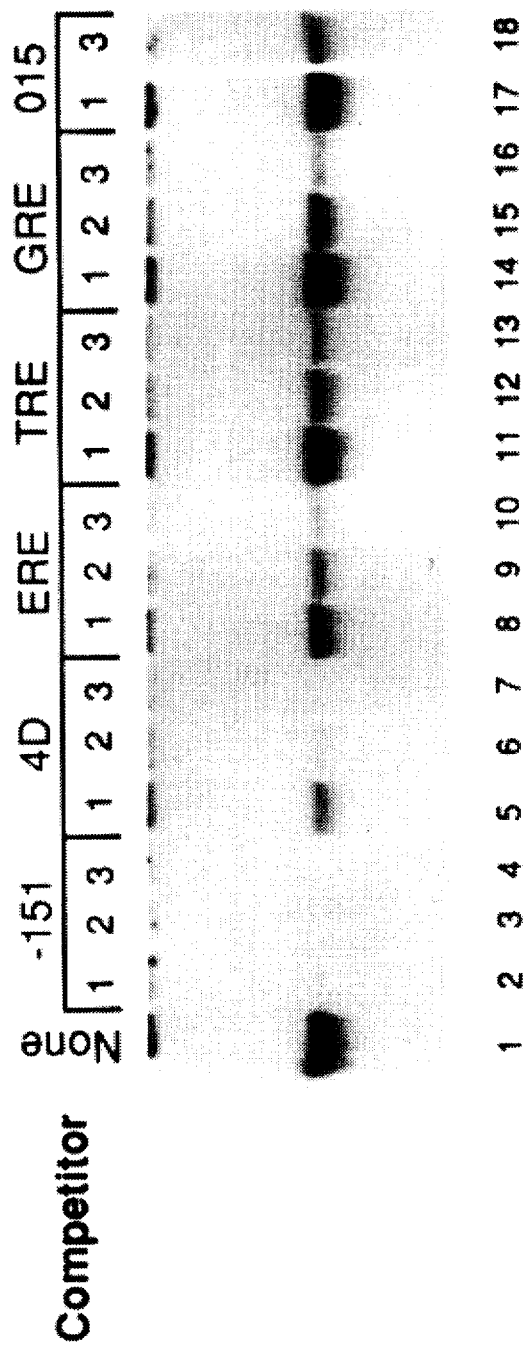

FIG. 9—HNF-4 Does Not Significantly Bind ERE, TRE or GRE

Mobility-shift assay using purified HNF-4 (MonoQ, Fxn 38, 0.03 µl) in the presence of 3 µg BSA, 50 ng poly dl-dC, $^{32}$P-labeled, −151 to −130 TTR [probe (0.5 ng) and unlabeled oligonucletides as competitors as indicated: −151—= −151-130 TTR, 4D =NHF4D and GRE, TRE and GRE are the estrogen, thyroid hormone and glucocorticoid response elements (see Table 1). 0.015 is an unrelated oligonucleotide, 5'-GATCCTCGGGAAAGGGAAACCGAAACT-GAAGCC-3'(SEQ ID NO. 8). 1, 2 and 3 are 50-, 250- and 500-fold molar excess, respectively.

DETAILED DESCRIPTION

In accordance with this detailed description, the following definitions apply:

Expression control sequence—a DNA sequence that controls and regulates the transcription and translation of another DNA sequence.

Operatively linked—a DNA sequence is operatively linked to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Antibody—an immunoglobulin molecule or functional fragment thereof, such as Fab, F(ab')$_2$ or dAB. An antibody preparation is reactive for a particular antigen when at least a portion of the individual immunoglobulin molecules in the preparation recognize (i.e., bind to) the antigen. An antibody preparation is nonreactive for an antigen when binding of the individual immunoglobulin molecules in the preparation to the antigen is not detectable by commonly used methods.

Standard hybridization conditions—salt and temperature conditions substantially equivalent to 5×SSC and 65° C. for both hybridization and wash.

DNA sequences—The DNA sequences of this invention refer to DNA sequences prepared or isolated using recombinant DNA techniques. These include cDNA sequences, DNA sequences isolated from their native genome, and synthetic DNA sequences. The term as used in the claims is not intended to include naturally occurring DNA sequences as they exist in nature.

HNF-4 (hepatocyte nuclear factor 4) is a protein enriched in liver extracts that binds to sites required for the transcription of the transthyretin (TTR) and apolipoprotein CIII (apoCIII) genes (Costa et al., 1989; Costa et al., 1990; Leff et al., 1989). HNF-4 protein (54 kD) has been purified and a cDNA clone isolated encoding the protein. HNF-4 is a member of the steroid hormone receptor superfamily with an unusual amino acid in the conserved "knuckle" of the first zinc finger (DGCKG). This and the fact that HNF-4 does not bind significantly to estrogen, thyroid hormone or glucocorticoid response elements indicate that HNF-4 may represent a new subfamily. HNF-4 binds to its recognition site as a dimer and activates transcription in a sequence-specific fashion in nonhepatic (HeLa) cells. HNF-4 mRNA is present in kidney and intestine as well as liver but is absent in other tissues. DNA binding data suggest that HNF-4 could be identical to liver factor A1 (LF-A1), a factor previously shown to regulate the transcription of the $\alpha$-1 antitrypsin, apolipoprotein A1 and pyruvate kinase genes.

As used herein, the word "ligand" means a substance which.. binds to a receptor, such as a hormone or growth substance. Inside a cell the ligand binds to a receptor protein, thereby creating a ligand/receptor complex, which in turn can bind to an appropriate hormone response element. Single ligands may have multiple receptors. For example, both the $T_3R_\alpha$ and the $T_3R_\beta$ bind thyroid hormone such as $T_3$. The ligand can be an agonist or an antagonist.

As used herein, the word "operative", in the phrase "operative hormone response element functionally linked to a ligand-responsive promoter and an operative reporter gene", means that the respective DNA sequences (represented by the terms "hormone response element", "ligand-responsive promoter" and "reporter gene") are operational, i.e., the hormone response element can bind with the DNA-binding domain of receptor protein (either wild-type or chimeric), the ligand-responsive promoter can control transcription of the reporter gene (upon appropriate activation by a HRE/-receptor protein/ligand complex) and the reporter gene is capable of being expressed in the host cell. The phrase "functionally linked" means that when the DNA segments are joined, upon appropriate activation, the reporter gene (.e.g., CAT or luciferase) will be expressed. This expression occurs as the result of the fact that the "ligand responsive promoter" (which is downstream from the hormone response element, and "activated" when the HRE binds to an appropriate ligand-/receptor protein complex, and which, in turn then "controls" transcription of the reporter gene) was "turned on" or otherwise activated as a result of the binding of a ligand-/receptor protein complex to the hormone response element.

As used herein, the phrase "DNA-binding domain" of receptors refers to those portions of the receptor proteins (such as glucocorticoid receptor, thyroid receptor, mineralocorticoid receptor, estrogen-related receptor and retinoic acid receptor) that bind to HRE sites on the chromatin DNA. The boundaries for these DNA-binding domains have been identified and characterized for the steroid hormone superfamily. See FIG. 8; also see Giguere et al. (1986); Hollenberg et al. (1987); Green and Chambon (1987); and Miesfield et al. (1987), Evans (1988).

The present transcription factor is believed to play a regulatory role in the formation of lipid carrying proteins such as Apo CIII, as well as possible effects on Apo A1, Apo B, pyruvate kinase, $\alpha$1 antitrypsin and glutamine synthetase. The cDNA sequence has been identified, and the invention relates to the DNA sequence, recombinant molecules based thereon, probes, sense and antisense RNA, and appropriately transformed host cells. Diagnostic and therapeutic applications are likewise contemplated.

Of particular interest herein is the APF1 receptor and its gene, since these structures are useful for assessing the activity of drugs.

Numerous epidemiological studies have shown that altered plasma lipoprotein levels are associated with coronary heart disease risk. Elevated low-density lipoprotein (LDL) levels and decreased high-density lipoprotein (HDL) levels are associated with increased coronary heart disease. Studies conducted in many laboratories over the last 30 years have defined a rather complex set of events that determine plasma lipoprotein levels.

Apolipoprotein CIII is a constituent of VLDL and HDL and comprises ~50% of VLDL protein and 2% of HDL protein. Human plasma apoCIII concentrations are in the range of 0.12–0.14 mg/ml. ApoCIII is a glycoprotein containing 1 mol each of galactose, galactosamine, and either 0, 1, or 2 mol of sialic acid. The three resultant isoproteins recognizable by isoelectric focusing are designated CIII-0, CIII-1, and CIII-2 and comprise 14, 59, and 27% of plasma apo CIII, respectively. In vitro apoCIII has been shown to inhibit the activities of both lipoprotein lipase and hepatic lipase. ApoCIII has also been shown to decrease the uptake of lymph chylomicrons by the perfused rat liver. These in vitro studies suggest that apo CIII might delay catabolism of triglyceride-rich lipoproteins. Recently, hypertriglyceridemic subjects were shown to have circulation lipoprotein and nonlipoprotein inhibitors of lipoprotein lipase. The lipoprotein-associated inhibition correlated best with apo CIII concentration. In the same study, apoCIII was shown to be a noncompetitive inhibitor of the activity of partially purified lipoprotein lipase. In addition, patients with combined apo A-I and apoCIII deficiency were shown to have low plasma triglyceride levels, and in vivo studies showed that they rapidly convert VLDL to LDL. In vitro lipolysis of their VLDL was inhibited by added apoCIII. Thus, it appears that primary abnormalities in the quantity or quality of apoCIII may affect plasma triglyceride levels, and the physiological role of apoCIII may be in the regulation of the catabolism of triglyceride-rich lipoproteins. Functional domains of apoCIII have been demonstrated. The COOH-terminal 39 amino acids bind phospholipid, whereas the $NH_2$-terminal 40 amino acids do not. Synthesis of apoCIII is mainly in liver and to a lesser degree in intestine.

It is apparent that there is a wide variety of medical uses for agonists and antagonists of HNF-4 and apoCIII. For example, diseases involving the cardiovascular system, such as atherosclerotic heart disease, hyperlipidemia and arteriosclerosis can be treated by interfering with the deposition of VLDL and cholesterol in the vessels.

Similarly, liver disease involving the presence of excessive lipid levels can be treated.

Other disease conditions in which the ligands to HNF-4 and agonists/antagonists to apoCIII will be apparent to those skilled in the medical arts, using such compounds in art-recognized doses.

Likewise, conditions such as obesity may be treated in this manner.

Ligands to HNF-4 may be evaluated which have pharmaceutical properties. One assay format which can be used which employs two genetic constructs. One is typically a plasmid that continuously expresses the receptor of interest when transfected into an appropriate cell line. CV-1 cells are most often used. The second is a plasmid which expresses a reporter, e.g., luciferase under control of a receptor/ligand complex. For example, if a compound which acts as a ligand for HNF-4 is to be evaluated, one of the plasmids would be a construct that results in expression of the HNF-4 receptor in an appropriate cell line, e.g., the CV-1 cells. The second would possess a promoter linked to the luciferase gene in which an HNF-4 response element is inserted. If the compound to be tested is an agonist for the HNF-4 receptor, the ligand will complex with the receptor and the resulting complex binds the response element and initiates transcription of the luciferase gene. In time the cells are lysed and a substrate for luciferase added. The resulting chemiluminescence is measured photometrically. Dose response curves are obtained and can be compared to the activity of known ligands.

Other reporters than luciferase can be used including CAT and other enzymes.

Viral constructs can be used to introduce the gene for the receptor and the reporter. The usual viral vector is an adenovirus. For further details concerning this preferred assay, see U.S. Pat. No. 4,981,784 issued Jan. 1, 1991 hereby incorporated by reference, and Evans et al., WO88/03168 published on 5 May 1988, also incorporated by reference.

HNF-4 antagonists can be identified using this same basic "agonist" assay. A fixed amount of an antagonist is added to the cells with varying amounts of test compound to generate a dose response curve. If the compound is an antagonist, expression of luciferase is suppressed.

The APF1 gene can also be incorporated into the assay described above. Agonist ligands can be screened by the continuous expression of receptors, and by evaluating ligand binding to the receptors, and thereafter quantitating the production of the reporter.

Genes for chimeric receptors can be used in the assay system. These chimeric receptors have hybrid functional characteristics based on the "origin" of the "parental" DNA-binding and ligand-binding domains incorporated within the chimeras. For example, if the DNA-binding domain in the chimeric receptor is a retinoic acid receptor DNA-binding domain (i.e., is obtained from wild-type retinoic acid receptor or is a mutant that contains the functional elements of retinoic acid DNA-binding domain), then the chimera will have DNA-binding properties characteristic of a retinoic acid receptor. The same is true of the ligand-binding domain. If the ligand-binding domain in the chimeric receptor binds to thyroid hormone, then the chimera will have ligand-binding properties characteristic of a thyroid hormone receptor. Most often this is done for a so-called orphan receptor, i.e., one where the natural ligand is unknown. The chimerics usually constructed are ones in which the ligand binding domain of a gene for a known receptor, for example, a glucocorticoid receptor, as replaced by the ligand binding domain of the orphan. The resulting construct generates a receptor with the ligand binding domain of the orphan and the DNA binding domain of the glucocorticoid receptor. Thus, the receptor can be used to control a glucocorticoid controlled gene. Ligands to the orphan are thereby screened in an otherwise well developed system. The HNF-4 gene can be used in this manner.

Genes for the receptors in expression systems can also be employed which are capable of producing large amounts of a receptor which can be purified and used in binding assays. These assays are done in a competitive format in which the suspect ligand competes for receptor with a quantity of a known, labeled ligand. These assays can be used to confirm that the ligand does bind the receptor, and as further confirmation that the results of the cis/trans assay are not artifacts. The systems used to express large amounts of receptors include virally infected cells in which the gene for the receptor is introduced by a viral construct by infection rather than by plasmid transfection. Adenoviruses are preferred. Also, a yeast based system can be used where the receptor gene is inserted into a plasmid suitable for yeast expression.

The gene for HNF-4 receptors may be inserted, for example, into a viral construct, and the viral vector with HNF-4 receptor genes can be used to over-express receptors for HNF-4 as well as in the convection form of the assay noted above.

Expression of recombinant DNA molecules according to this invention may involve post-translational modification of a resultant polypeptide by the host cell. For example, in mammalian cells expression might include, among other things, glycosytation, lipidation or phosphorylation df a polypeptide, or cleavage of a signal sequence to produce a mature protein. Accordingly, as used herein, the term HNF-4 encompasses full-length polypeptides and modifications or derivatives thereof, such as glycosylated versions of such polypeptides, mature proteins, polypeptides retaining a signal peptide, truncated polypeptides having comparable biological activity, and the like.

mRNA can be isolated from cells expressing HNF-4, and used to create a cDNA library. Many methods are known for isolating mRNA and for producing cDNA from it. (See, e.g., Gubler and Hoffman, 1983 and Maniatis et al., 1982.)

The cDNA is then inserted into an appropriate vector. The vector pcDM8, described by Brian Seed (Seed, 1987) is representative. This plasmid has several advantages including a high copy number in E. coli, a eukaryotic promoter, and high level of expression in transient expression systems such as COS 7 cells. However, several other vector systems are available. (See, e.g., Cate et al., 1986.)

After constructing a cDNA library, the next step is to isolate from it clones containing HNF-4 cDNA sequences. There are currently many ways to isolate cDNA for a differentially expressed mRNA. These include, for example, (1) plus/minus screening with labeled cDNA; (2) production of subtracted cDNA libraries; and (3) screening with subtractive cDNA probes. (Davis, 1986; Sargent, 1987; Davis et al., 1985, Hedrick et al., 1984; and Duguid et al., 1988.)

Different techniques can be used to identify clones that contained cDNA for HNF-4 sequences. In a first method, clones can be tested for expression of HNF-4 activity in an appropriate eukaryotic expression system. One can use a variety of direct expression techniques, including antibody screening of fusion proteins encoded by cDNA cloned in λGT11 (Young and Davis, 1983; Young and Davis, 1984); or activity assay of oocyte-conditioned media after injection of mRNA from cloned cDNA, or from plasmid or phage DNA carrying SP6/T7 promoters. Alternatively, one can make libraries in plasmid, phage, and cosmid vectors containing a variety of promoter, selection and replication elements. Animal cells may be transfected with the library for transient or stable expression. Transfection can be accomplished by a variety of methods. For transient expression, investigators have used spheroplast fusion, DEAE dextran, and electroporation. For stable expression they have used calcium phosphate, spheroplast fusion, and electroporation.

Until recently, identification of cloned molecules by direct expression has required sensitive assays and has been restricted to lymphokines. However, cDNA cloning of single-chain cell-surface molecules in efficient transient expression vectors (see, e.g., Seed and Aruffo, 1987 and Seed, 1987), either by antibody "panning" technology (Wysocki and Sato, 1978) or by identification of functional molecules by FACS (Yamasaki et al., 1988), has expanded the range of cloned molecules that one can identify by direct expression.

Genomic DNA sequences, including transcriptional promoters, for HNF-4 can be isolated by screening genes. A human genomic library with $^{32}$P-labeled probes derived from the coding regions of the HNF-4 DNA sequences. This may yield clones that contain portions of the untranscribed and untranslated regions of the HNF-4 gene.

Transcriptional promoters have a number of uses. First, they are useful to construct vectors which can be used to induce expression of HNF-4. Such vectors may be useful, for example, in gene transfer assays, wherein the inducible promoter is positioned so that it drives transcription of a reporter gene such as chloramphenicol acetyltransferase (CAT), beta-galactosidase, luciferase, etc. This construct can then be introduced transiently or in stable form into an appropriate mammalian cell line. Potential inhibitors or stimulators of induction can then be assayed by measuring their effect on induction by any or all of the inducers listed above.

Hybridomas producing monoclonal antibodies which recognize HNF-4 can also be produced.

Investigators are also exploring radioimmunotherapy and immunotoxin therapy. Radioimmunotherapy involves the use of radioimmunoconjugates in which nuclides such as $^{125}$I, $^{90}$Y, $^{186}$Re and the like are bound to antibodies recognizing a particular surface antigen. Immunotoxins are antibodies conjugated with cell toxins, such as Pseudomonas exotoxin and the like. Upon injection, these conjugated antibodies target the toxic agents to cells expressing the antigen. In accordance with this invention, radioactive markers, nuclides and cellular toxins may be conjugated with HNF-4, or antibodies recognizing HNF-4, target cells expressing HNF-4 or ligands thereto.

An alternative method for isolating HNF-4 would employ fluorescent-antibody labeling. In this method, HNF-4 expressing cells are incubated with Moabs (monoclonal antibodies) and then the Moabs are labeled with, e.g., fluorescently tagged anti-mouse antibody. Cells binding the fluorescent antibodies may then be sorted with a fluorescence activated cell sorter (FACS). The DNA from the sorted cells may be used to transform a bacterial host such as E. coli. DNA from the resulting colonies may then be used to transform a bacterial host such as E. coli. DNA from the resulting colonies may then be used to transfect an appropriate cell line, and this procedure may be repeated until a single expressing clone is identified.

An expression library may also be created in E. coli. For example, a λ ZAP® (Stratagene)/HL-60 library may be constructed and used to express the inserted DNA in E. coli. After plating, the plaques can be directly screened with, e.g., radioactively labeled monoclonals (Young and Davis, 1983 and Young and Davis, 1984). The plaques to which the monoclonals bind can be picked and the DNA insert isolated from them.

Another method to identify HNF-4 ligands, not based on antibody recognition, is to transfect COS 7 cells with an appropriate library, that may be subtracted, and then pan them directly into HNF-4 expressing cells. Once again, multiple rounds of panning may be required to enrich the library sufficiently to isolate the pertinent clones.

Another technique for isolating the DNA sequences involves screening a cDNA library with oligonucleotide probes. If sufficient HNF-4 protein is purified, for example by affinity chromatography using immobilized antibody, one may determine a partial amino acid sequence and synthesize oligonucleotide probes that correspond to at least a portion of the gene. These probes may then be used to screen the CDNA library. Alternatively, the oligonucleotides may be used as primers to generate long probes to be used in screening the library for genes.

Several uses for HNF-4 DNA sequences and molecules are contemplated as being part of the present invention. First, one may use HNF-4 to produce monoclonal antibody preparations that are reactive for these molecules. The Moabs may be used diagnostically or in turn as therapeutic agents to inhibit HNF-4 binding.

Second, one may use a soluble form of HNF-4 or fragments thereof as a binding inhibitor. The HNF-4 peptides would bind to the HNF-4 ligands and the HNF-4 ligand would bind to HNF-4 receptors. Both methods would thereby inhibit HNF-4 binding.

To produce recombinant soluble HNF-4 ligand, one could, for example, alter a DNA encoding those molecules to eliminate the transmembrane region. Thus, DNAs for soluble molecules would include all or part of the extracellular domain, perhaps attached to the cytoplasmic domain. This approach has already been validated using soluble CD4, the surface protein on T-cells that binds to the AIDS virus (Fisher et al., 1988). This approach also avoids the problems of antibody therapy, since the polypeptides used would be less likely to induce an immune response.

One problem investigators have encountered with soluble recombinant molecules is a short in vivo plasma half-lie (Capon et al., 1989). Because such molecules are quickly cleared from the system, large doses or frequent injections are necessary to have a therapeutic effect. Therefore, investigators have sought methods to increase the half-life of soluble molecules. A potential solution is to link the soluble molecule to another molecule known to have a longer half-life in the blood stream. Due to their long half life, immunoglobulin molecules are promising candidates. Capon et al. (1989) have described the linking of soluble CD4 to an immunoglobulin molecule using recombinant DNA techniques. In this approach, one replaces the variable region of an immunoglobulin molecule with the soluble protein, forming a protein/immunoglobulin fusion protein.

It is expected that the recombinant soluble immunoglobulin fusion proteins will have greater plasma half-life than the soluble protein alone. Such fusion proteins are preferably produced with recombinant constructs, fusing a DNA sequence encoding the soluble molecule to a DNA sequence encoding the constant domain of an immunoglobulin molecule. The recombinant DNA may then be expressed in an approrpiate host cell, preferably an animal cell, to produce the fusion protein.

Immunoglobulin fusion proteins have another advantage. Because immunogglobulin molecules are normally bivalent (i.e., they have two binding sites), an immunoglobulin fusion protein would have two HNF-4s and so, two ligand binding sites. Therefore, one would expect them to have greater affinity or avidity for cells displaying HNF-4 ligands.

Third, one may use molecules binding to HNF-4 receptors (such as anti-HNF-4 antibodies, or markers such as the ligand or fragments of it) to detect the presence of disease. This involves, for example, making a molecule detectable by fluorescence or radioactivity, administering it to a patient and determining where in the body it accumulates. In this way one could also identify the type of disease.

Fourth, if HNF-4 binds to its ligand through a carbohydrate moiety or some other post-translational modification, one could use HNF-4 to identify the carbohydrate on the HNF-4 ligand to which it is bound.

Fifth, one could use HNF-4 as part of a system to screen small molecules for inhibitors. For example, one could create an assay system in which small molecules are tested for the ability to inhibit the interaction between HNF-4 and ligands thereto. Small molecule inhibitors identified in this way would provide drug candidates.

Sixth, one could use these molecules to identify endogenous proteins that inhibit HNF-4.

Seventh, one can generate fusion proteins. It is known that proteins are composed of several structural domains (Simmons et al., 1988). DNA sequences encoding various domains of each protein are fused using, for example, the genetic fusion techniques described for making immunoglobulin fusion proteins. The domains chosen are those having the ability to bind to ligands and HNF-4. Domains binding to known ligands would be preferable. The polypeptides produced on expression of these DNA sequences are useful because they would block adhesion of any cell having a ligand to either the HNF-4 receptor, the ligand or both.

Finally, one could use HNF-4 and HNF-4 ligand DNA sequences to produce nucleic acid molecules that intervene in HNF-4 or HNF-4 ligand expression at the translational level. This approach utilizes antisense nucleic acid and ribozymes to block translation of a specific mRNA, either by masking that mRNA with an antisense nucleic acid or cleaving it with a ribozyme. These methods will also be useful in treating disease conditions.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into HNF-4-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAS, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mMA species, and eighteen base recognition sequences are preferable to shorter recognition sequences.

The DNA sequences described herein may thus be used to prepare antisense molecules against, and ribozymes that cleave, mRNAs for HNF-4 and HNF-4 ligands.

Antisense molecules and ribozymes may be used in methods to treat disease by introducing into cells molecules that interfere with the expression of HNF-4. Since therapeutic agents can be delivered easily by intravenous injection, hepatocytes are attractive targets for such therapies, provided the antisense molecules or ribozymes can be delivered effectively.

Investigators have suggested two approaches which could be used to deliver these molecules to target cells. The first involves transfecting the target cell with a vector that expresses the anti-HNF-4 antisense nucleic acid or the HNF-4-specific ribozymes as an mRNA molecule (Hambor et al., supra). While this approach is very useful when dealing with cell lines in vitro, it may not be as effective in vivo. A second approach that is more promising for in vivo delivery involves loading liposomes with anti-HNF-4 antisense molecules, HNF-4-specific ribozymes or vectors which express them. These liposomes could also contain monoclonal antibodies to direct the liposome to the site of disease.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and Synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other-phage DNA, e.g., M13 and Filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early and late promoters of SV40 or adenovirus, the lac system, the trp system, the TAC or TRC system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

Antibodies against HNF-4 and ligands thereto will make possible another method for isolating other ligands. The method takes advantage of an antibody characteristic known as idiotypy. Each antibody contains a unique region that is specific for an antigen. This region is called the idiotype. Antibodies, themselves, contain antigenic determinants; the idiotype of an antibody is an antigenic determinant unique to that molecule. By immunizing an organism with antibodies, one can raise "anti-antibodies" that recognize them, including antibodies that recognize the idiotype. Antibodies that recognize the idiotype of another antibody are called anti-idiotypic antibodies. Some anti-idiotypic antibodies mimic the shape of the original antigen that the antibody recognizes and are said to bear the "internal image" of the antigen (Kennedy, 1986). When the antigen is a ligand, certain anti-idiotypes that bind to receptors for insulin, angiotensin II, adenosine I, β-adrenalin, and rat brain nicotine and opiate receptors (Carlsson and Glad, 1989).

Taking advantage of this phenomenon, other HNF-4 ligands may be isolated using anti-idiotypic antibodies. Anti-idiotypes may be used to screen for molecules binding to the original antigen.

EXPERIMENTAL PROCEDURES

Extract preparation and chromatography were carried out at 4° C.

Preparation of Rat Liver Nuclear Extract

Crude rat liver nuclei extracts were prepared using the method of Gorski et al. (1986) modified as follows: approximately 50 gm of tissue were removed from 3 to 4 freshly sacrificed male rats (Sprague-Dawley, about 20 weeks old), homogenized in 30 ml of buffer A (10 mM HEPES pH 7.9, 25 mM KCl, 0.15 mM spermine, 0.5 mM spermidine, 1.0 mM EGTA, 1.0 mM EDTA, 1 mM dithiothreitol (DTT), 0.32M sucrose), dounced 5 to 7 times (pestle A) and diluted with two volumes of Buffer b (as A except 2M sucrose). 27 ml of the homogenate were layered on a 10-ml cushion of Buffer B and centrifuged in a Beckman SW27 rotor at 15 krpm for 45 min. The pelleted nuclei were rinsed once in buffer C (as buffer A except 20% glycerol in place of sucrose), dounced 5 times (pestle B) and brought to 0.41M KCl with buffer D (as C except 1M KCl). The protein was extracted by gentle rocking at 4° C. for 45 minutes. The chromatin was pelleted by centrifugation at 180,000×g for 45 min. and the supernatant (crude nuclear extract, 3.5–5.0 mg/ml protein) was frozen immediately in liquid $N_2$ and stored at −80° C. DTT and protease inhibitors (phenylmethyl-sulfanyl fluoride, 0.5 mM; benzamidine HCl, 1 mM; leupeptin, 0.5 µg/ml; pepstatin, 1 µg/ml) were added to all buffers just prior to use.

Mobility-shift Assay and Purification of HNF-4

Gel mobility-shift (DNA binding) assays (Fried & Crothers, 1981) were carried out in 15 µl reactions in shift buffer (20 mM HEPES (pH 7.9), 40 mM KCl, 2 mM $MgCl_2$, 1 mM DTT, 0.5 mM EGTA, 4% Ficoll) and contained 1–2 µl protein extract and 0.5 ng double-stranded oligonucleotide probe labeled with $^{32}p$ by Kenow. Reactions were incubated at room temperature for 20 minutes. Poly (dI-dC), oligonucleotide competitor and bovine serum albumin (BSA) were added as indicated. Protein-bound DNA complexes (5 µl of shift reaction) were separated from free probe by electrophoresis on an 8% polyacrylamide gel in 25 mM Tris-borate, 0.25 mM EDTA at 4° C.

Chromatography fractions were assayed by the mobility-shift assay using either the APF-1 or HNF4P oligonucleotide as probe. Crude nuclear extract (up to 300 mg) was applied to a 60 ml heparin agarose (Sigma, Type 1) column equilibrated in buffer E (20 mM HEPES pH 7.9, 10% glycerol, 1 mM DTT, 0.1 mM EDTA, 0.1 Mm EGTA) containing 150 mM KCl. The column was developed with a 400 ml linear gradient from 0.2 to 0.8M KCl. Fractions with HNF-4 activity (0.50–0.55M KCl) were pooled, precipitated with ammonium sulfate (300 mg/ml final), dissolved in buffer F (as buffer E but with 0.05% Nonidet P-40 (NP-40)) containing 100 mM NaCl, dialyzed and loaded onto a 240 ml Sephacryl S300 (Pharmacia) column. Active fractions, eluting just after the void volume, were loaded onto a 5 ml double-stranded DNA cellulose (Sigma) column equilibrated in buffer F/100 mM NaCl. The column was developed with a three-step gradient: 150 mM, 300. mM and 1M NaCl. Active fractions (eluting at 300 mM NaCl) were diluted to 100 mM NaCl and poly (dI-dC) and sonicated, denatured salmon sperm DNA were added to 10 µg/ml each. After 10 minutes on ice, the sample was loaded onto a 2 ml HNF4P oligonucleotide affinity column prepared as in Kadonaga and Tjian (1986) and equilibrated in buffer F/100 mM NaCl. The column was developed with a 20 ml linear gradient from 0.1 to 1.0M NaCl. Active fractions, eluting at 0.18–0.3M NaCl, were diluted to 0.1M NaCl, supplemented with poly (dl-dC) and salmon sperm DNA to 3 µg/ml each and passed over a 2 ml APF1 oligonucleotide affinity column as described above. The HNF-4 binding activity, eluting at 0.25 to 0.5M NaCL, was dialyzed against buffer T (as buffer F but with 20 mM Tris HCl pH 8.0 and 20% glycerol) containing 100 mM NaCl and loaded onto a FPLC Mono Q HR 5/5 (Pharmacia) column. The column was developed with a linear gradient from 0.1 to 1.0M NaCl. The peak fraction in one preparation (fraction 38) eluted at about 0.42M NaCl. Purified HNF-4 refers to material passed over all five columns.

Renaturation of HNF-4

Approximately 50 ng of purified HNF-4 (based on binding activity to APF1 oligonucleotide) were mixed with SDS sample buffer, heated for 15 min. at 72° C. and fractionated on a 12.5 cm 10% SDS-polyacrylamide gel (Laemmli, 1970) pre-run with 0.1 mM sodium thioglycolate. Gel slices were cut out and the protein was eluted and renatured essentially as described by Briggs et al. (1986) except that 0.1 mg/ml BSA was added to the elution buffer and buffer G (as buffer E but with 0.1% NP-40) containing 100 mM NaCl and 3.5 mM $MgCl_2$ and 6M guanidine-HCl were used for renaturation. 5 µl of 35 µl recovered material was used in the mobility shift assay (0.05 µg poly (dl-dC).

DNA Footprinting, Phosohatase and Protease Studies

A 137-bp DNA fragment containing −202 to −70 of the mouse TTR promoter (see Costa et al., 1986) was labeled with $^{32}P$ by filling in with Klenow either at a BamH 1 site (7 bp from −202) or at an Xba 1 site (−70). Purified HNF-4 (enough to shift 2 ng of APF1 oligonucleotide) was incubated in a 30 µl shift reaction with 10 ng of the −202/−70 TTR probe in the absence of poly dl-dC and electrophoresed on a 5% polyacrylamide gel. After treating the gel with 1,10-phenanthroline copper ion as described in Kuwabara and Sigman (1987), the bound and free probes (identified by autoradiography of the wet gel) were cut out, embedded in agarose and the DNA was recovered by electroelution onto DEAE membrane (NA-45 (Schleicher & Schuell)). The cleaved probes were analyzed on an 8M urea/10% polyacrylamide gel.

For the phosphatase reaction, purified HNF-4 (MonoQ fxn 38, 4 ng) was incubated for 20 min. at 37° C. in a 20 µl, reaction either with or without calf intestine alkaline phosphatase (CIP, 2.5 µl at 1U/µl Boehringer Mannheim) in 0.25×Shift buffer lacking KCl and EGTA but containing 0.005% NP-40 and 0.25 µg/ul BSA. The reaction without enzyme contained 2.5 µl of the CIP storage buffer (30 mM triethanolamine pH 7.6, 3M NaCl, mM $MgCl_2$, 0.1 mM $ZnCl_2$). For the protease reactions, purified HNF-4 (fxn 38, 62.5 ng) was incubated for 1.5 hours at 37° C. in a 10 µl reaction with Protase V8 (5 ng) or Endoproteinase LysC (5 ng) (both from Boehringer Mannheim) in 0.5×butter T containing 100 mM NaCl. One-fifth of each reaction was tested in the mobility-shift assay (BSA at 3 µg/15 µl reaction, no poly (dl-dC) with each of four $^{32}P$-labeled oligonucleotide probes (APF1, −151 to −130, HNF4P, HNF4D).

Cyanogen Bromide Cleavage and Protein Sequencing

Approximately 10 µg (200 pmoles) of purified HNF-4 (fxn 38) was brought to 1.3M guanidine HCL (ultra pure, ICN) and 0.03% β-mercaptoethanol (Sigma) and loaded onto a reverse-phase HPLC column (Aquaporebutyl 30×2.1 mm, 7 µm, Brownlee labs) equilibrated in buffer H (5% 1-propanol in 10 mM trifluoroacetic acid, TFA). The column was developed with a 9 ml-gradient from 5% to 59% 1-propanol in 10 mM TFA at a flow rate of 0.15 ml/min. Fractions containing HNF-4 (47% to 50% propanol) were pooled, dried, and treated with 5 µg/ml CNBr in 50% formic acid for 24 hours. The CNBr-generated peptides were separated by HPLC using the conditions given above. Fractions containing peptides were either sequenced directly on an Applied Biosystems gas phase (Model 470) sequenator (pep 1, pep 2 and pep 5) or further purified on a 16.5% SDS polyacrylamide gel and processed for sequencing as in Matsudaira (1987) (pep 3 and pep 4).

Isolation of HNF-4 cDNA Clones

Oligonucleotide primers corresponding to the least degenerate regions of pep 1, pep 2 and pep 3 were synthesized: Primer 1S (from sense direction of pep 1) was 5'CC(C/A)tcc(C/G)AXGGNGCNAAYYTNAA-3' where N=A+G+T+C, X=A+G, Y=C+T. Primer 1A (antisense of pep 1) was 5'- TTAggTTNGCNCCYT(G/C)N(G/C)XNGG-3'. Primer 2S (sense of pep 2) was 5'-CATCTAGAATtGAgCAgAT(Y/A)CA(G/A)TTYAT(Y/A)AA-3'. Primer 2A (antisense of pep 2) was 5'AACGTCAGAgcTT(X/T)AT(G/A)AAY-TG(X/T)ATYTGYTC-3'. Primer 3S (sense of pep 3) was 5'-GAgGCtGTNCAXAAYGAX(C/A)GNGA-3'. Primer 3A (antisense of pep 3) was 5'-TC(Y/G)C(G/T)cTCXTTYTG-NACNGCYTC—. Lower case letters indicate codon usage according to Lathe (1985); underlined regions indicate an Xho 1 restriction site used for subcloning. The primers were used in the polymerase chain reaction (PCR) (Saiki et al., 1988) in pairwise combinations (Primer 1S+2A, 1S+3A, etc.) following the protocol by Perkin-Elmer Cetus. 50 µl-reactions containing 0.5 to 4 µg of each primer (1S and 1A, 4 µg; 2S and 2A, 0.5 µg; 3S, 1 µg; 3A, 1.5 µg) and 10 µl of rat liver cDNA library in λ Zap II (from Strategene, $1.5×10^6$ independent recombinants, amplified and used at $4×10^{10}$ pfu/ml) underwent 30 cycles in a DNA Thermal Cycler (Perkin Elmer Cetus). Each cycle consisted of 1 min. at 94° C., 1 min. at 57° C., 2.5 min. (plus 5 sec/cycle) at 72° C. PCR products were cloned into the polylinker region of Bluescript KS(+) (Stratagene) and sequenced using the Sequenase kit from U.S. Biochemicals. dITP reactions were performed on regions where the sequence was ambiguous.

The nonamplified rat liver cDNA library (Stratogene) was screened for full length clones as described in Maniatis et al. (1982) except: the nitrocellulose filters were autoclaved to bind the DNA; no formamide was used in the prehybridization buffer; and hybridization and washings were done at 50° C. The probe was the subcloned PCR product obtained with Primers 3S and 2A labeled with $^{32}P$ by random priming (Feinberg & Vogelstein, 1983).

Transactivation Assay

The HIV-CAT reporter construct (~5 kb) contained −57 to +80 of the human immunodeficiency virus (HIV) long terminal repeat (LTR) (Rosen et al., 1985) immediately 5' to the bacterial chloramphenicol acetyl transferase (CAT) gene linked to the SV40 splice and poly(a) sites (from pSV2 CAT, Gorman et al., 1982) in pGEM-1 (Promega) (construction described in Lew, Decker, Stehlow, Darnell, in preparation). The APF1-HIV-CAT reporter construct consisted of two APF1 oligonucleotides in direct repeat cloned into the Sma 1 site of the pGEM polylinker (17 bp form the HIV LTR) of HIV-CAT. The HNF-4 expression vectors (sense, pLEN4S, and antisense, pLEN4A) were constructed by cloning the entire 3 kb HNF-4 cDNA of pf7 into the BamH 1 site of pLEN (courtesy of Cal-Bio Inc.) pLEN is a ~5 kb expression vector containing the SV40 enhancer (1120-bp, Hind III fragment), the human metallothionein promoter (836-bp, Hind III-BamH1 fragment) and human growth hormone 3' untranslated region (~550-bp, BamH I-EcoR I (fragment) in pUC8.

DNA transfections and β-galactosidase and CAT assays were performed essentially as in Sambrook et al. (1989). DNA was transfected into HeLa cells, grown in Dulbecco's-Modified Eagle's medium (DMEM, Gibco) plus 10% bovine calf serum (BCS, Hyclone), using the calcium phosphate method. A precipitate of HNF-4 expression vector (pLEN4S or PLEN4A, 0 to 5 µg), 1 µg pCMV-β(gal) (internal control, MacGregor & Caskey, 1989), 2 µg reporter construct (HIV-CAT or APF1-HIV-CAT) and 50 µg denatured sonicated salmon sperm DNA were added to cells 60–80% confluent in a 100-mm dish. After 15 hrs. at 37° C., the cells were treated with a glycerol shock (15%) and incubated for 48 hours at 37° C. in DMEM plus 10% BCS and 10 mM sodium butyrate (to enhance expression from the SV40 enhancer, Gorman et al., 1983). Extracts were prepared, normalized to β-galactosidase activity and assayed for CAT activity (20-hr. incubation at 37° C.).

Northern Blot Analysis

Total RNA was extracted from male rat (Sprague-Dawley) tissue using the acid phenol method of Chomezynski and Sacchi (1987) as modified by Puissant and Houdebine (1990). Poly A+ RNA was selected on oligo-dT cellulose columns and electrophoresed (5 µg/lane) in a 1% agarose formaldehyde gel as described in Sambrook et al. (1989). The RNA was transferred to Immobilon-N (Millipore) and probed according to the protocol provided by the manufacturer. HNF-4 mRNA was detected with a random-primed cDNA fragment containing nucleotides 616 to 1114 (the hatched area in FIG. 3, top). The high stringency wash was with 0.2×SSC, 0.1% SDS at 600° C. for 15 minutes. The autoradiograph with the HNF-4 probe was exposed for 3 days with two intensifying screens. Ribosomal RNA (28S and 18S, 4.9 and 1.9 kb, respectively) was used as size markers.

Table 1

The sequence and origin of the top strand of the oligonucleotides used are given. The underlined nucleotides were added for convenience. Complementary bottom strands had four-base overhands at their 5' ends. The bold type highlights the region of consensus and shows matches in the hormone response elements. ERE is from the Xenopous vitellogenin A$_2$ (Klein-Hitpaβ et al., 1986), TRE and GRE are palindromic variants of the response elements in the rat growth hormone (Glass et al., 1988) and tyrosine aminotransferase (Strahle et al., 1987) genes, respectively. Arrows indicate conserved palindromic regions.

TABLE 1

| | Gene | Sequence | Position |
|---|---|---|---|
| −151 to −130 | TTR | 5'-TCGAGGCAAGGTTCATATTTGTGTAG-3' | −151 to −130 (mouse) |
| HNF4P | TTR | 5'-TCGACCCTAGGCAAGGTTCATATGGCC-3' | −156 to −138 (mouse) |
| HNF4D | TTR | 5'-TCGACTCTCTGCAAGGGTCATCAGTAC-3' | −1.86 kb (mouse) |
| APF1 | apoCIII | 5'-TCGAGCGCTGGGCAAAGGTCACCTGC-3' | −66 to −87 (human) |
| LF-A1 | α1-AT | 5'-AGCAAACAGGGGCTAAGTCCACTGGCTG-3' | −101 to −128 (human) |
| HNF-4 Consensus | | GGCAAAGGTCAT<br>T  T G TC  C | |
| Hormone Response Elements | | | |
| ERE (estrogen) | | 5'-AGCTCTCAGGTCACTGTGACCTGA-3' | |
| TRE (thyroid) | | 5'-AGCTCTCAGGTCATGACCTGA-3' | |
| GRE (glucocorticoid) | | 5'-AGCTCTCAGAACACTGTGTTCTGA-3' | |

RESULTS

Purification and Characterization of HNF-4 Protein

Table 1 lists the different oligonucleotides used in the purification and characterization of the HNF-4 binding protein. Oligonucleotide −151 to −130 contains the HNF-4 site (−151 to −140) required for TTR expression in transfection assays as well as a weak HNF-3 site (−130 to −140) (Costa et al., 1989); HNF4P is similar to −151 to −130 but does not contain the HNF-3 site; HNF4D is from a distal site in the TTR promoter (approximately −1.9 kb) which was shown to enhance the transcription of TTR marginally (Costa et al., 1988; 1989) and which is bound less well by protein in crude liver extracts than HNF4P. APF1 and LF-A1 are oligonucleotides derived from the promoter regions of the human apolipoprotein CIII (apoCIII) and α1-antitrypsin (α1-AT) genes, respectively. Cross competition studies done previously (Costa et al., 1990) showed that the factor that binds to the HNF-4 Site in the TTR promoter also binds to APF1.

HNF-4 binding protein was purified from rat liver nuclear extract by six chromatography steps including sequence-specific DNA affinity columns made with either multimeric HNF4P or APF1 oligonucleotides. Each step was assayed by the mobility-shift assay using a double-stranded probe (HNF4P or APF1). An SDS gel of the starting material of the last five columns plus the final purified fraction (Fxn 38, FIG. 1A) showed a single Coomassie-stained band of 54 kD nominal molecular weight that co-purified with the mobility-shift activity. In one preparation, approximately 700 mg nuclear protein from 41 rats yielded 30–40 μg of the 54 kD protein with an overall recovery of 10–15% based on the mobility-shift activity. By comparing protein concentration and DNA-binding activity (APF1 probe) for each step of the purification, the cumulative gain in specific activity was estimated to be 5000 to 10,000-fold.

To show that the 54 kD species was the HNF-4 binding protein, the purified material was subjected to preparative SDS-PAGE, the gel was cut into slices and the proteins were eluted from each slice, renatured and assayed for HNF-4 binding activity. One such renaturation experiment in which only the 45 to 65 kD region was assayed showed that the major band migrating at 54 kD (primarily slice 3) contained HNF-4 binding activity (FIG. 1B). Other experiments (not shown) verified that the regions below 45 kD and above 65 kD did not contain binding activity.

Figure 1A:
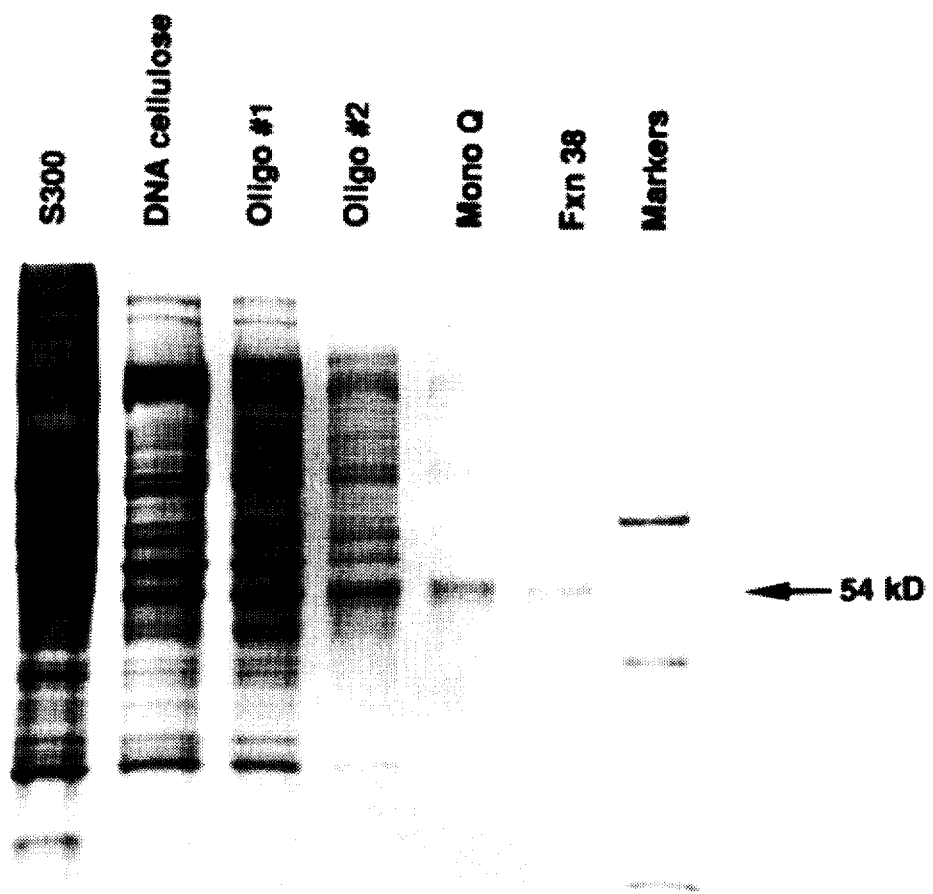
FIG. 1—Purification and Identification of HNF-4
Figure 1B:
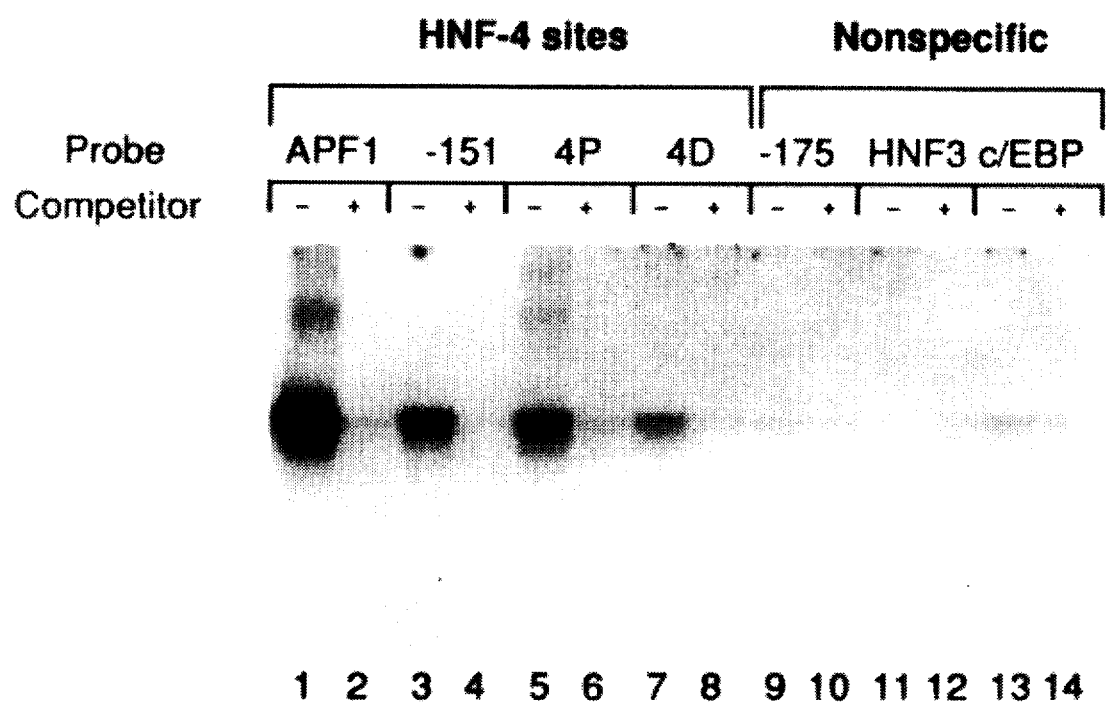

The affinity column containing the apoCIII site, APF1 (oligo #2, FIG. 1A) was used in the purification scheme after the column with the TTR site, HNF4P (oligo #1, FIG. 1A). Therefore, to be certain that the final purified material still bound the TTR site, four different probes containing slightly different HNF-4 sites (APF-1, −151 to −130, HNF4P, HNF4D) and three probes lacking sequence similarity to the HNF-4 recognition site (−175 to −151, HNF3 and C/EBP) were labeled to the same specific activity and tested in the mobility-shift assay with the purified protein. The purified material bound to all four HNF-4 sites and product identical shift bands (FIG. 1B). The different relative affinities of the purified material for the various probes (APF1 >−151 to −130=HNF4P >HNF4D) is the same as that found in crude liver nuclear extracts (not shown). As expected, the purified material did not bind to any of the unrelated oligonucleotides (FIG. 1B, lanes 9–14).

Figure 2A:
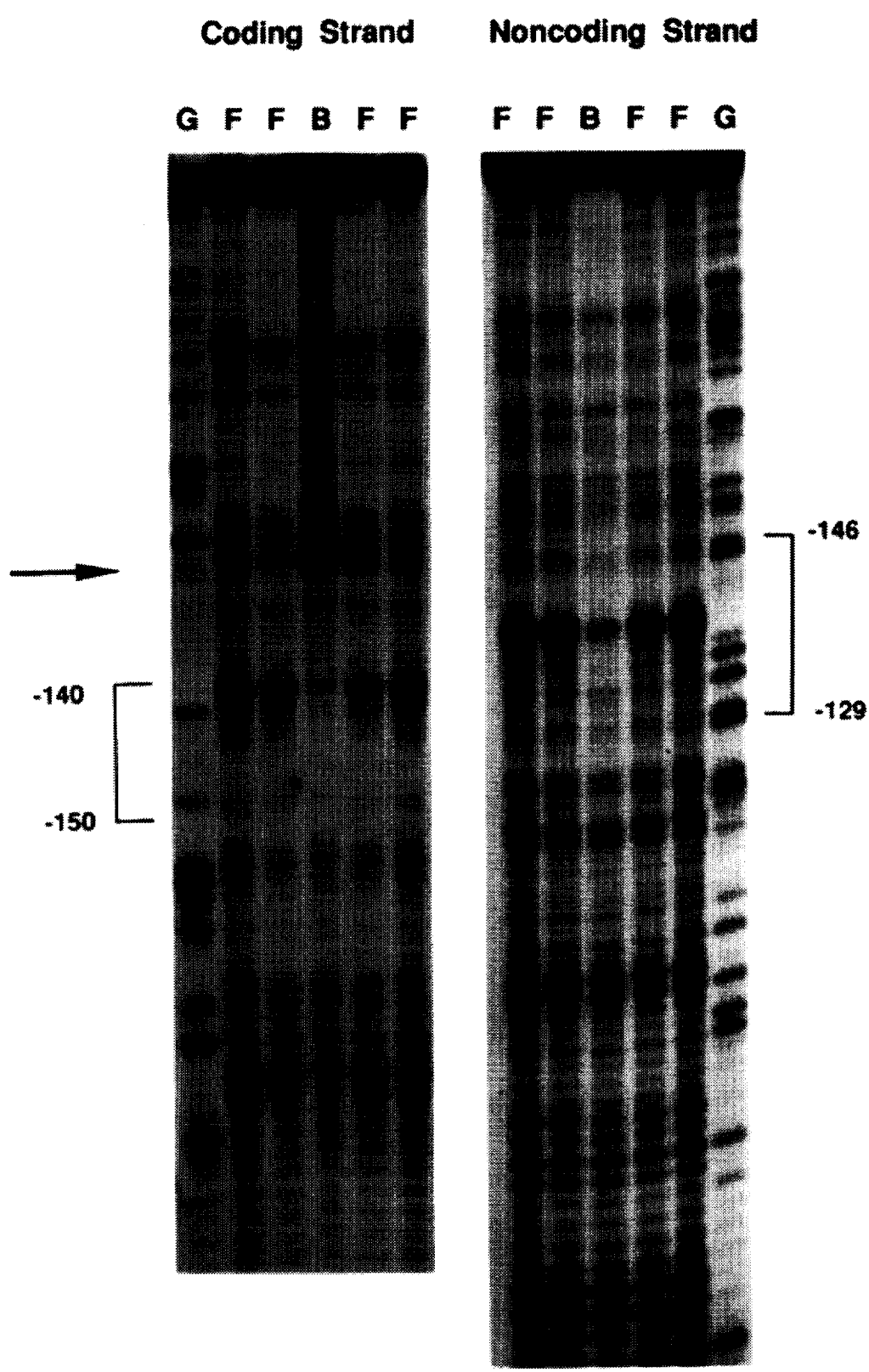

To verify that the protein we purified was the one originally described by Costa et al. (1989), the purified protein was shown to protect the region from −140 to −150 of the coding strand in the TTR promoter from cleavage by copper phenanthroline (FIG. 2A). This is the same region originally defined as the HNF-4 site by transient transfection assays with deletion mutants and by methylation interference experiments with crude liver extracts (Costa et al., 1989).

Figure 1C:
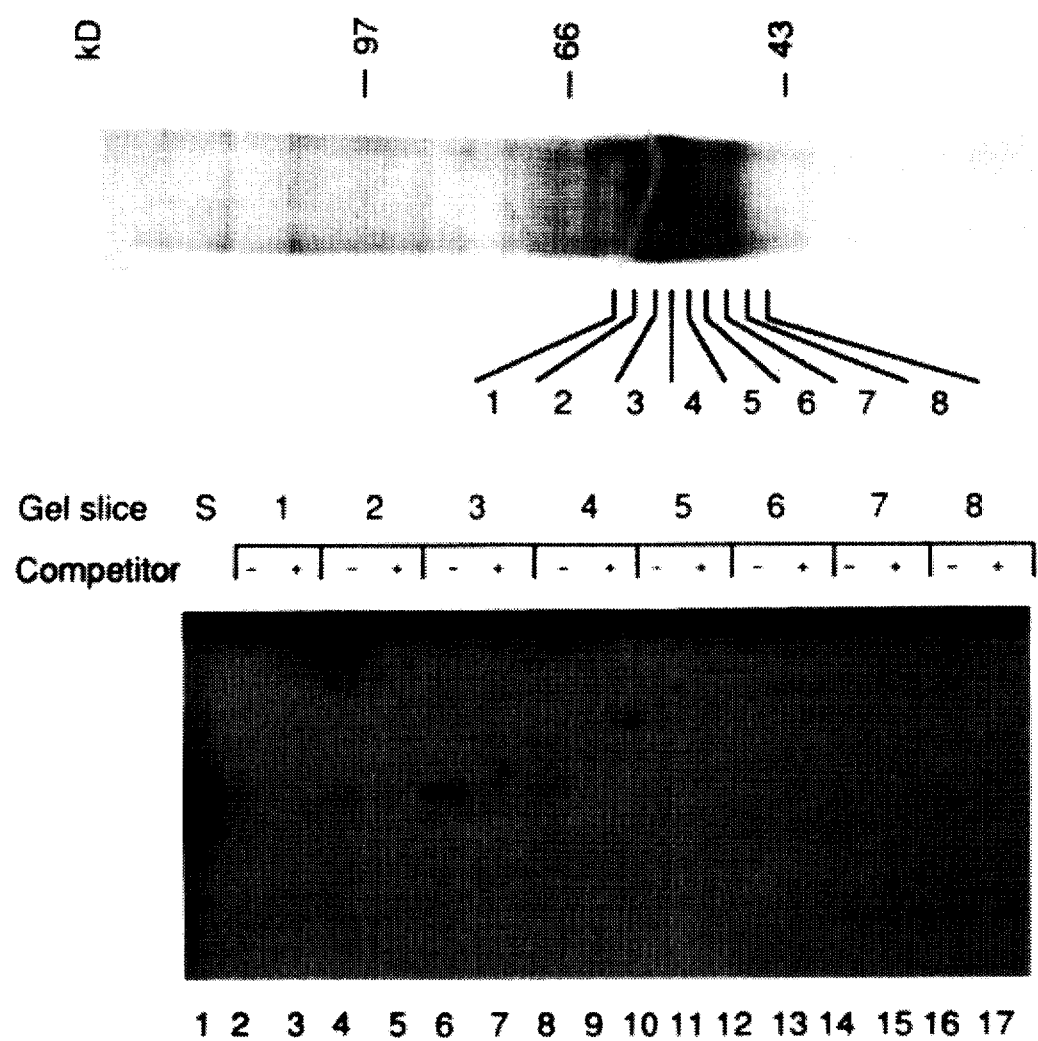
Figure 2B:
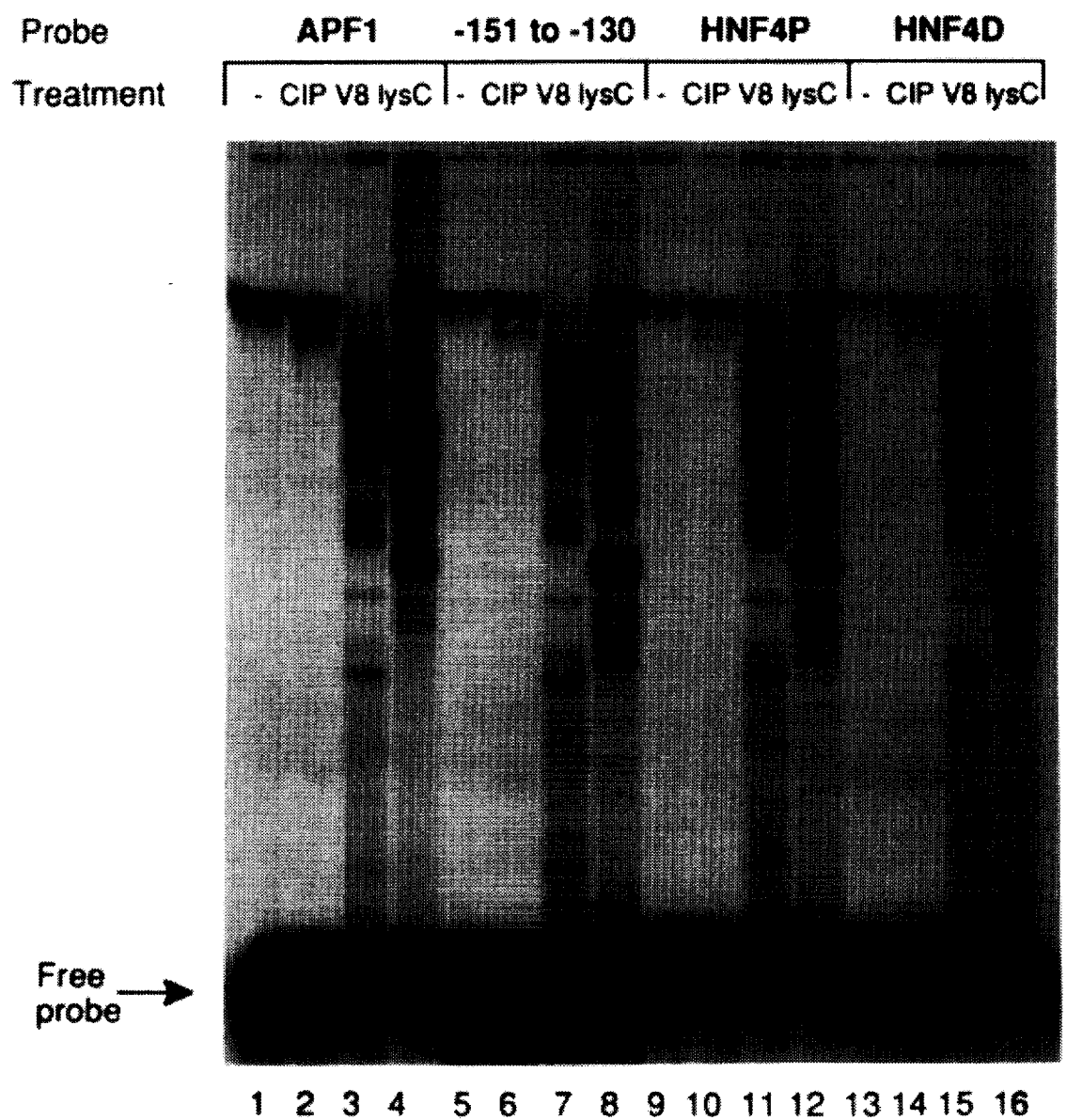

The appearance of minor bands migrating slightly faster than the major band at 54 kD in some silver-stained SDS gels (evident as a broad band in FIG. 1C) and the fact that the purified material bound several somewhat different probes raised the concern that there might be more than one DNA binding protein present in the purified material. To examine this possibility, Mono Q fraction 38 was treated with a modifying reagent (phosphatase or one of several proteases), divided into aliquots and subjected to the mobility-shift assay using the four HNF-4 probes described above. The results, displayed in FIG. 2B, show that a given treatment (calf intestine alkaline phosphatase (CIP), Protease V8 (V8), Endoproteinase Lys-C (lysC)) created essentially the same pattern of shifted bands-regardless of the probe used. Had the purified material contained a mixture of different polypeptides, different peptide fragments, and therefore different shift bands, should have resulted. Therefore, we concluded that there was a single polypeptide in the purified material that bound to the various probes.

Isolation of HNF-4 cDNA Clones

In order to isolate the cDNA encoding HNF-4 protein, a partial amino acid sequence of the protein purified from the rat liver was obtained. Since the intact protein was found to be N-terminally blocked, the purified material (Mono, fxn 38; 10 μg) was subjected to reverse-phase high pressure liquid chromatography (HPLC) and the major peak, containing the 54 kD protein, was cleaved with cyanogen bromide. The resulting peptides were separated by HPLC and sequenced.

Five peptide sequences were obtained (pep 1–5). Sense (S) and antisense (A) primers 23 nucleotides long with degeneracies ranging from 36 to 4096 were made to three of the peptides (pep 1, pep 2, pep 3). The primers were used in pairwise combinations (primers 1S and 2A, 1A and 2S, etc.) in a polymerase chain reaction (PCR) with an amplified rat liver cDNA library a the template. Only the combinations of primers 1S and 2A and primers 3S and 2A resulted in products easily discernible by ethidium-bromide staining of an agarose gel (1.0 and 0.5 kilobase, kb, respectively). After subcloning and sequencing, the large product (1S+2A) was found to contain the smaller product (3S+2A) (FIG. 3, top). The deduced amino acid sequence from the large product also contained a region very similar to the two zinc fingers found in steroid hormone receptors. The shorter PCR product, which did not contain the zinc fingers, was used to screen $3.6 \times 10^5$ primary recombinants in the rat liver library. Of 22 positive clones at the second round of screening, nine were fully characterized and found to be overlapping.

The partial nucleotide sequence of the largest cDNA insert (pf7, FIG. 3 bottom) contains a long open reading frame of 1365 base pairs (bp) starting with an initiator methionine at nucleotide 59. There is another in-frame ATG codon beginning at nucleotide 32 but comparison with the consensus sequence for translation initiation (GCC A/G CCATGG, Kozak, 1987) and SDS-PAGE analysis of in vitro translation products (not shown) suggest that the ATG codon at nucleotide 59 is the major initiator for translation. All five peptide sequences derived from the purified HNF-4 protein appeared in the predicted amino acid sequence (FIG. 3 bottom) confirming that the purified HNF-4 preparation did indeed contain only one major polypeptide. The 1365-bp open reading frame encodes a protein 455 amino acids long with molecular weight of 50.6 kD. The polyadenylation signal was not found.

A search of GenBank revealed that HNF-4 is a novel protein but that it has a structure analogous to that of the steroid/thyroid hormone receptors (see FIG. 4). HNF-4 contains a region with two potential zinc fingers between amino acids 50 and 116 which is 40 to 63% identical to the zinc finger (DNA binding) domain of other members of the steroid receptor superfamily. The proposed regulatory protein for the mouse major histocompatibility class I proteins (H-2RIIBP (Hamada et al., 1989) had the greatest similarity (62.7% identity) and the human thyroid hormone receptor (c-erbA; $T_3T_\beta$) (Weinberger et al., 1986) was the second most similar (59.7% identity) in this region. While the zinc finger domain of HNF-4 is flanked by regions with no similarity to any known protein, there is a large hydrophobic region in the C-terminal half of the protein (amino acids 133 to 373) which has definite similarity to the ligand binding domain of some of the other receptors (20–37% identity). Again, HNF-4 is most similar to H-2RIIBP (37.3% identity) but as with H-2RIIBP, it is not known if HNF-4 requires a ligand let alone what the ligand might be.

The HNF-4 protein has two other distinctive features: a proline-rich region (23%) at the C-terminus (amino acids 400–477) which could be an activator domain (Mermod et al., 1989) and three serine/threonine-rich regions (30–38%) scattered throughout the molecule (amino acids 15 to 44, 129 to 161, and 398 to 426) which could be sites for phosphorylation (Krebs et al., 1988). Whether or not HNF-4 is modified has not been established yet, but the possibility of some post translational modification is suggested by the somewhat aberrant mobility of the protein isolated from rat liver in the SDS gel (54 kD versus 50.6 kD predicted from amino acid sequence) as well as the appearance of minor bands migrating slightly faster than the major band in SDS gels.

In Vitro Expression of HNF-4 cDNA

Figure 5A:
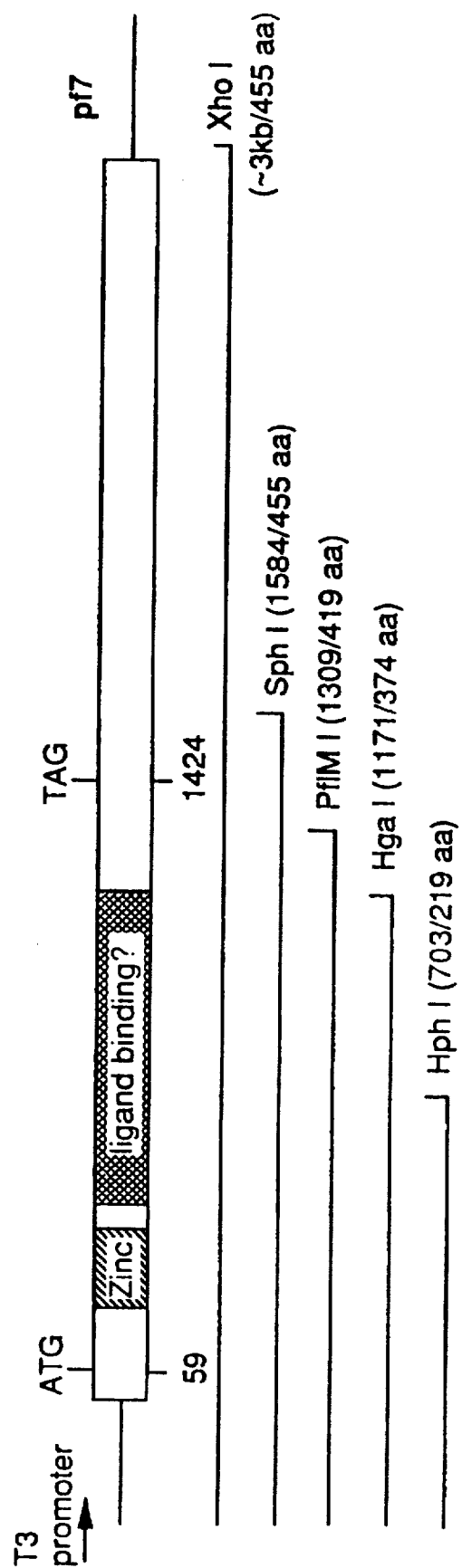
Figure 5B:
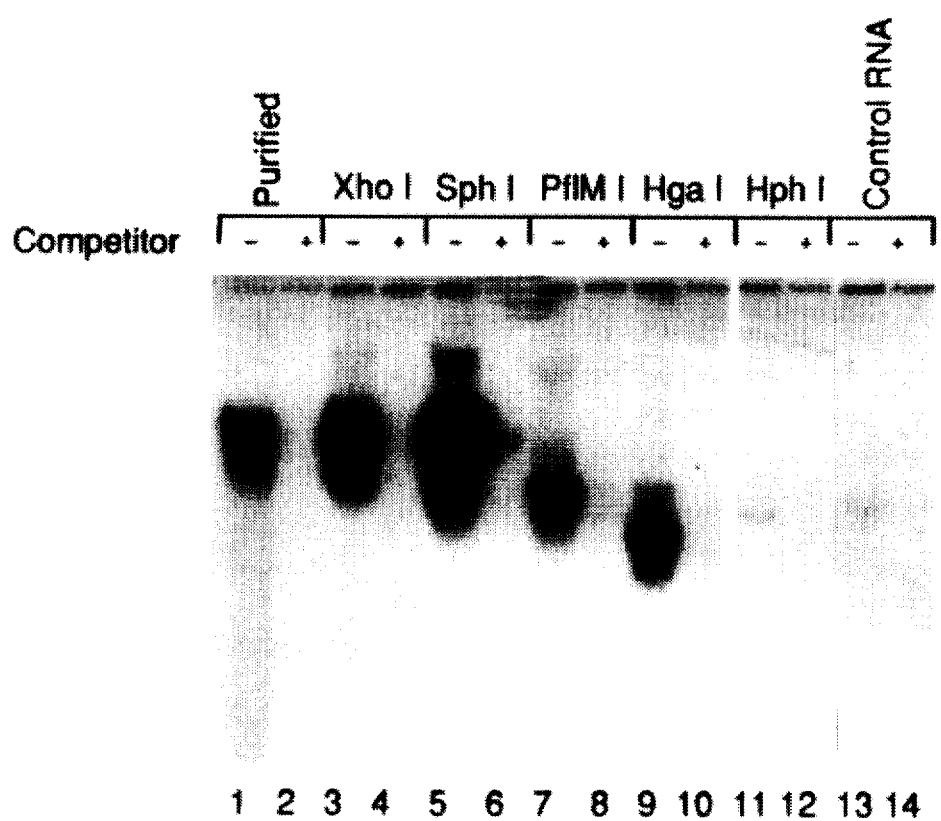
Figure 5C:
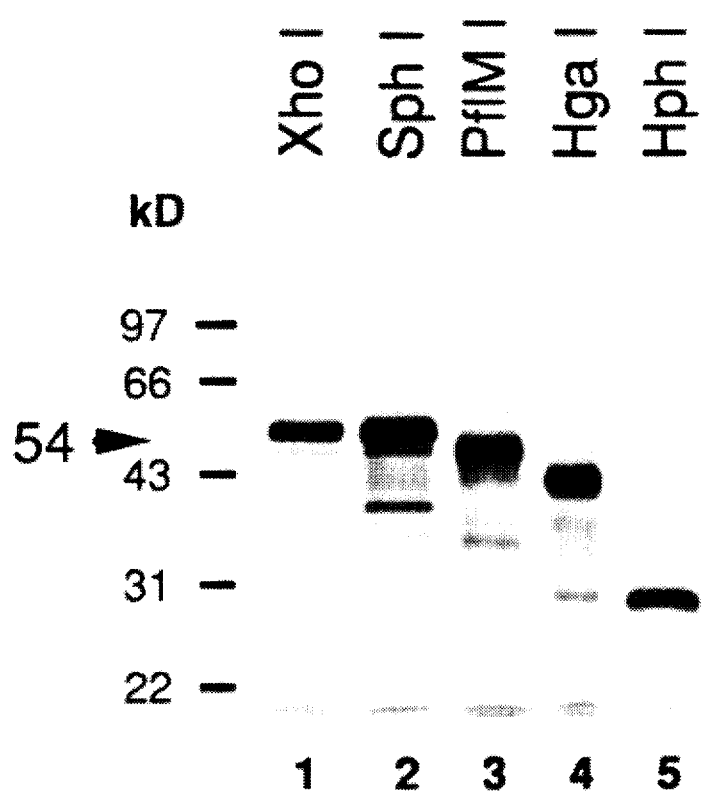
Figure 5D:
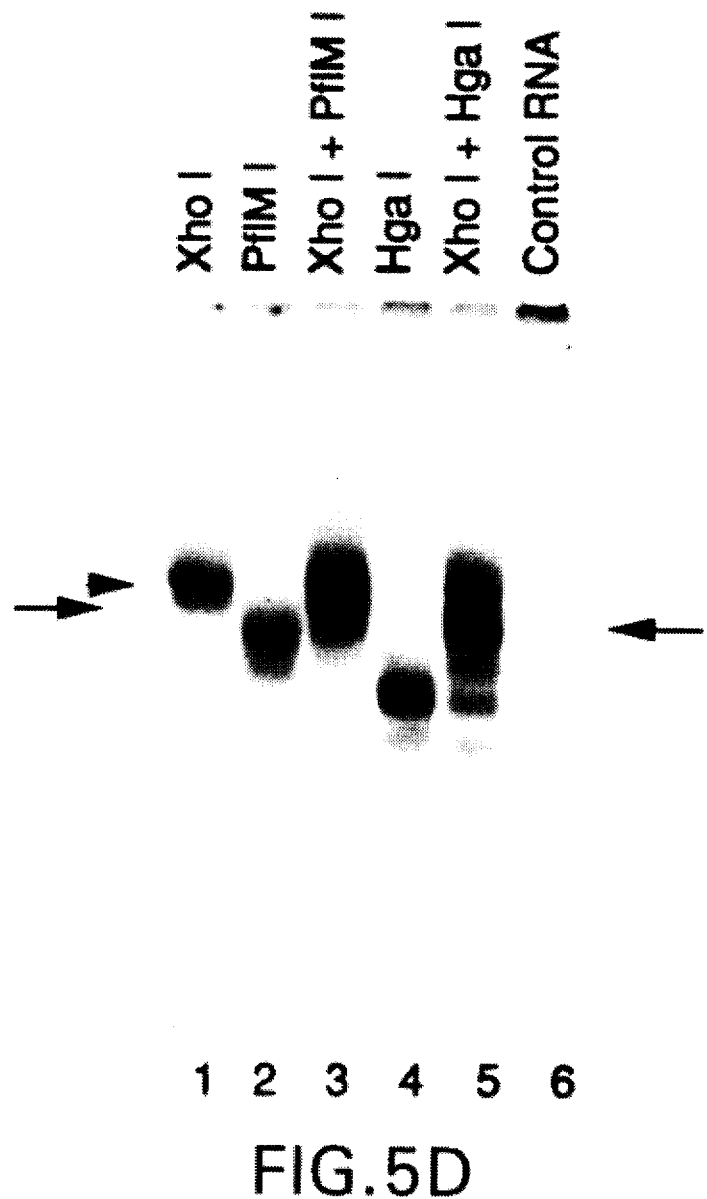

To verify that the cDNA clone pf7 encoded the HNF-4 binding protein, T7 RNA polymerase transcripts were produced and translated in vitro and the resulting protein was tested in the mobility-shift assay. The protein synthesized in vitro bound the APF-1 oligonucleotide in a sequence-specific manner (lanes 3 and 4, FIG. 5B) with the shifted complex migrating at a position identical to that of the complex formed with the material purified from rat liver (compare lane 3 to 1, FIG. 5B). The position of the stop codon was confirmed by cutting the pf7 cDNA at unique restriction sites either before (PflM 1, nucleotide 1309) or after (Sph I, nucleotide 1584) the proposed stop codon (nucleotide 1424) and then synthesizing the protein in vitro and preforming a mobility-shift assay. The product of the template cut with Sph I produced a complex similar to that produced by the full-length cDNA (Xho I), but the PflM I-cut template yielded a faster moving complex (lanes 3, 5, 7; FIG. 5B). Analysis of the protein products on an SDS gel showed that the product from the Sph I-cut template was the same size as that from the full length template (compare lane 2 to 1, FIG. 5C) and that both migrated at a position roughly equivalent to that of the purified rat nuclear protein—54 kD. The product of the PflM I-cut template migrated faster, confirming the prediction that it should be 36 amino acids (4000 daltons) shorter (lane 3, FIG. 5C). Plasmid template cut with Hga I (at nucleotide 1171) produced an even shorter protein product (by 45 amino acids, 5175 daltons) (lane 4, FIG. 5C) which gave rise to a faster migrating shift complex (lane 9, FIG. 5B). When the truncated in vitro translation products were tested for DNA binding to an oligonucleotide containing another HNF-4 site, HNF4P, identical results were obtained (gel not shown). The results of the in vitro translation experiments confirm that the pf7 cDNA encodes a protein that binds to the HNF-4 recognition site in a fashion analogous to that of the purified protein.

HNF-4 Binds to Its Recognition Site as a Dimer

Further examination of translation products produced from truncated cDNA templates showed that a polypeptide containing amino acids 1 to 219 (Hph I-cut, lane 5, FIG. 5C) did not bind DNA even though the entire zinc finger region, the DNA binding domain of the receptors, was present (lane II, FIG. 5B). Thus, the region between amino acid 219 and 374, the possible ligand binding domain, might be required for binding of the HNF-4 protein to its recognition site. Since amino acids in the ligand binding domain of the estrogen receptor are known to be necessary for receptor dimerization and subsequent DNA binding (Kumar & Chambon, 1988; Fawell et al., 1990), we determined whether HNF-4 binds to its recognition site as a monomer or as a dimer. The full length cDNA (Xho I) was co-translated in vitro with either of the two truncated products that bind DNA (PflM I and Hga I) and the products were tested in the mobility-shift assay. When the full length and truncated transcripts were translated together, complexes of intermediate mobility were produced with both the APF-1 probe (lanes 3 and 5, FIG. 5D) and the −151 to −130 TTR probe (not shown). These intermediate bands were most likely produced by heterodimers between the full length and truncated proteins which suggests that the shift complex that was monitored consists of a homodimeric protein bound to the probe. Since no shift complexes corresponding to monomers were detected with either the in vitro translated or the purified protein and since the transcript lacking the proposed domain (Hph I) did not bind the probe at all, we conclude that protein dimerization is required for HNF-4 to bind to its recognition site.

Transcriptional Activation by Cloned HNF-4

Since deletion of the HNF-4 binding site in the TTR promoter severely reduced transcription of transfected templates (Costa et al., 1989), we determined whether HNF-4 produced from the cloned cDNA would activate transcription of a target gene. An expression vector containing HNF-4 cDNA was cotransfected into HeLa cells with constructs containing a reporter gene, chloramphenicol acetyl transferase (CAT), which either did or did not contain HNF-4 recognition sites (APF1-HIV-CAT and HIV-CAT, respectively). The results are shown in FIG. 6. The HNF-4 expression vector containing the cDNA in the sense orientation stimulated CAT production from the reporter constructs only when the HNF-4 sites were present (compare lanes 2–4 to lanes 6–8, FIG. 6). The vector containing the cDNA in the antisense orientation, on the other hand, did not activate CAT expression above background (compare lanes 9–11 to lane 1, FIG. 6). Thus, we concluded that, under the conditions of these experiments, HNF-4 protein can activate transcription of a target gene. Furthermore, since the cells in which the activation occurred were non-hepatic in origin, no liver-specific post-translational modifications seem to be necessary for HNF-4 function.

Tissue Distribution of HNF-4 mRNA is Limited

HNF-4 binding activity was first found in liver. Since then, it has also been found in kidney and intestine but not in spleen or brain (Costa et al., 1990). To see if the tissue distribution of the HNF-4 binding activity reflected that of HNF-4 mRNA and to determine the size of the HNF-4 mRNA, a Northern blot analysis was performed. As shown in FIG. 7, the HNF-4 mRNA is present as a single species in rat liver, kidney and intestine but is absent in spleen, brain, white fat, lung and heart. This result supports the conclusion that HNF-4 is neither present exclusively in liver nor present in all tissues. The size of the mRNA was the same, −4.5 kB, in all rat tissues as well as in mouse liver (lane 1, FIG. 7). This is consistent with the fact that the pf7 clone isolated from the rat liver cDNA library contains a cDNA insert approximately 3 kb long but does not contain a polyadenylation site. A weak signal at approximately 2.3 kb was also seen (lanes 2, 3—FIG. 7). It varied in amount between blots; its relation to the major signal, if any, is not known.

HNF-4 Binds to an LF-A1 Site

LF-A1 is a liver-enriched factor that binds to a site required for transcription of human α1-antitrypsin (Monaci et al., 1988; HNF-2 in Li et al., 1988) certain apolipoproteins and other genes expressed in hepatocytes (Hardon et al., 1988; Vaulont et al., 1989). Since the LF-A1 sites are similar in sequence to the HNF-4 binding sites (see Table 1), we used the mobility-shift assay to test the affinity of the HNF-4 protein for one of the LF-A1 sites (FIG. 8). HNF-4 protein, either purified from rat liver or translated in vitro from the HNF-4 cDNA, bound the LF-A1 probe very well, producing a shift complex indistinguishable from those formed with the APF1 and HNF4P probes (compare lane 3 and 9 to 1 and 5 and 7 and 11, respectively—FIG. 8). In fact, the LF-A1 probe gave a stronger signal than the HNF4P probe (all probes were labeled to the same specific activity). To see whether the major protein species that binds the LF-A1 site in crude extracts is the same as that which binds the probe to purify HNF-4 protein, the mobility-shift assay was carried out with crude rat liver nuclear extracts. The results show that the major shift complex that was formed with the LF-A1 probe migrated at a position identical to that formed with the APF1 probe (compare lane 16 to 13, FIG. 8). In addition, the LF-A1 and APF1 complexes were specifically competed by each other (lanes 15 and 18, FIG. 8) and, as with the purified and in vitro produced HNF-4 protein, the LF-A1 site appeared to have a somewhat lower affinity for the factor than the APF1 site. Thus, it appears that HNF-4 could be identical to LF-A1.

HNF-4 Does Not Significantly bind ERE, TRE or GRE

Since the zinc finger region of HNF-4 is very similar to that of the thyroid and thyroid hormone receptors and since the APF1 site contains half of the palindrome found in those response elements (AGGTCA), we tested the HNF-4 protein for binding to estrogen, glucocorticoid and thyroid hormone response elements (ERE, GRE, TRE, respectively, see Table 1) by competition of these sites for labeled APF-1 probe. None of the three hormone response elements significantly blocked complex formation with the APF1 probe (gel not shown). since HNF-4 protein has a very high affinity for the APF1 site, we increased the sensitivity of the assay by using as a probe an oligonucleotide for which HNF-4 has a lower binding affinity, −150 to −130 TTR (see FIG. 1B). The results, shown in FIG. 9, indicate that the GRE and the TRE did not compete the complex formation by the −151 to −130 TTR probe significantly better than a completely unrelated oligonucleotide (O15; lanes 11–18). On the other hand, the ERE did compete slightly better than the unrelated oligonucleotide (compare lanes 8 and 19 to 17 and 18) but not nearly as well as the oligonucleotide containing the weakest HNF-4 site known to date (HNF4D) (compare lanes 8–10 to 5–7). Since all these competitions were in high molar excess (50-, 250- and 500-fold), we conclude that HNF-4 does not bind either the GRE, TRE or ERE to a degree which would be likely to be relevant in vivo.

DISCUSSION

The invention in its primary aspect comprises the protein purification of and the cloning and sequencing of a cDNA for a new tissue-restricted mammalian transcription factor termed hepatocyte nuclear factor 4 (HNF-4). HNF-4 was so named because its presence was first detected in liver extracts but not in extracts from several other tissues and its recognition site was distinct from that of three previously described proteins found mainly in the liver (Costa et al., 1989).

HNF-4—a Novel Member of the Steroid Hormone Receptor Superfamily

The deduced amino acid sequence of the HNF-4 protein indicates that it is a member of the steroid/thyroid hormone receptor superfamily, an ever increasing group of ligand-dependent transcription factors which possess a high degree of similarity in their DNA binding (zinc finger) domains. While HNF-4 is similar in sequence to the other factors in the zinc-finger domain, it could be a member of a new subfamily. The members of the superfamily have been classified according to the amino acid sequence in the knuckle of the first zinc finger (between $C_3$ and $C_4$) (referred to as the P Box) a region important in recognizing the sequence of the half site of the palindrome in hormone response elements (Danielson et al., 1989; Mader et al., 1989; Umesono & Evans, 1989; Forman & Samuels, 1990). For example, members of the thyroid hormone receptor (TR) subfamily contain amino acids EGCKG and bind to a TRE while members of the estrogen receptor (ER) subfamily contain amino acids EGCKA and bind to an ERE. The sequence of HNF-4 in this region (DGCKG) is most similar to that of the TR subfamily except that it contains an aspartic acid (D) in place of a glutamic acid (E) following $C_3$. This could explain why HNF-4 does not bind to a TRE (FIG. 9) even though it is almost identical (9/12 residues) to the HNF-4 consensus site. The significance, if any, of the very marginal binding of HNF-4 to the ERE (FIG. 9) is not known. While HNF-4 is the only factor published to date with the DGCKG sequence, considering the sizes of the other subfamilies, we anticipate that more will be found in the future (see receptors compiled in Umesono & Evans, 1989; Forman & Samuels, 1990; hap, de The et al., 1987; H-2RIIBP, Hamada et al., 1989; N10, Ryseck et al., 1989).

Like the well-characterized receptor proteins (estrogen, Kumar & Chambon, 1988; Fawell et al., 1990; thyroid hormone and retinoic acid, Forman et al., 1989; glucocorticoid Tsai et al., 1988), HNF-4 protein binds to its recognition site as a homodimer (FIG. 5D), even though that site lacks obvious dyad symmetry. Receptor dimerization in the other receptors has been localized to a series of heptad repeats of hydrophobic residues in the ligand-binding domain (Forman et al., 1989; Fawell et al., 1990; Forman & Samuels, 1990). The corresponding region in HNF-4 is also required for DNA binding (FIG. 5B) and contains at least twelve heptad repeats. Homodimer formation raises the possibility of heterodimer formation between HNF-4 and other transcription factors, as has been seen between the thyroid hormone and retionic acid receptors (Forman et al., 1989; Glass et al., 1989).

Since TTR expression is not dependent on hormone regulation, we did not anticipate that HNF-4 would fall into this ligand-dependent superfamily. However, its membership in this family and its limited homology to the ligand binding domains of other receptors with known ligands, raises the possibility that HNF-4 has an as yet unidentified ligand. Considering the number and variety of genes that HNF-4 controls (discussed below), the possibility of a ligand for HNF-4 is of considerable interest. Nonetheless, since so many other members of the superfamily fall into this category of "orphan receptors"—proteins for which no ligand has been identified (e.g., COUP-TF, Wang et al., 1989, ear2, Miyajima et al., 1988; ERR, Giguere et al., 1988;

H-2RIIBP, Hamada et al., 1989; N10, Ryseck et al., 1989), one must also entertain the possibility that these receptors have no ligands. Since the ligand binding domain overlaps with the dimerization domain, similarity in this region could have been maintained only for the purpose of dimerization and not for the purpose of binding a ligand.

HNF-4, LF-A1 and AF-1

LF-A1 is a liver-enriched factor originally identified in the α1-antitrypsin gene promoter (Li et al., 1988; Monaci et al., 1988) as a site conferring positive transcription regulation in vivo and in vitro. LF-A1 sites have been found also in the regulatory regions of the apolipoprotein A1 gene, haptoglobin-related genes (Hardon et al., 1988) and the pyruvate kinase L-type gene (Vaulont et al., 1989). In this paper we present DNA binding data that suggest that HNF-4 could be identical to LF-A1. However, since there are several examples of more than one factor binding to a given enhancer element, particularly among the hormone receptors (reviewed in Wingender, 1990; Ahe et al., 1985; Mueller et al., 1990; Schule et al., 1990; Umesono et al., 1988), positive identification of HNF-4 as LF-A1 must await further purification of LF-A1.

An example of a factor that appears to be distinct from HNF-4 but which has the same binding specificity as HNF-4, is AF-1 (apolipoprotein factor 1) which regulates the human apoCIII and apoB100 genes (Reue et al., 1988; Leff et al., 1989). While AF-1 purified from mouse liver binds to the −151 to −130 TTR oligonucleotide and footprints, the same region of the apoCIII promoter as does the purified HNF-4 protein, the tissue specificity and chromatographic properties of the two factors appears to be disparate (T. Leff, F. M. Sladek, unpublished observations). Regardless of whether HNF-4 is identical to or distinct from LF-A and AF-1, since HNF-4 binds to their recognition sites with relatively high affinity in vitro, one must consider the possibility that HNF-4 might also act on these sites in vivo. HNF-4 could be one of several potentially competing DNA binding proteins that interact with a series of related sites from a variety of genes transcribed in the liver.

HNF-4 and Liver-Specific Gene Expression

A primary objective of the present invention is to identify transcription factors that are themselves transcriptionally controlled in the liver. HNF-4 appears to be such a factor: HNF-4 can activate transcription in cells that are not of hepatic origin (FIG. 6) indicating that no liver-specific modifications are required for HNF-4 function, and HNF-4 mRNA is absent in many tissues (FIG. 7). These results, taken together with the demonstration that the rate of HNF-4 gene transcription is high in the liver but negligible in other tissues (Xanthopoulos, Prezioso, chen, Sladek, Darnell, in preparation), indicate that HNF-4, like HNF-3 (Lai et al., 1990) and C/EBP (Xanthopoulos et al., 1989), is a transcriptionally controlled transcription factor. Antecedent regulatory genes in a regulatory cascade can now be sought with confidence by studying the factors that regulate the genes that encode these regulatory proteins.

The investigation of tissue specific expression has ruled out, to a greater or lesser degree, two simple hypotheses which were entertained. First, there is no universal liver-specific transcription factor or group of transcription factors: HNF-1, C/EBP, HNF-3 and HNF-4 all have binding sites on several genes but none is a "master" positive-acting factor. Indeed, all of these factors are present in tissues other than liver and some are even in tissues not of the same germline as the liver (HNF-1, also in kidney and spleen, Baumeueter et al., 1990; C/EB, brain, fat, intestine, lung and skin, Birkenmeier et al., 1989; Xanthopoulos et al., 1989; Kuo et al., 1990; Ruppert et al., 1990; HNF-3A, intestine in small amounts; HNF-4, kidney and intestine, FIG. 7). In addition to varying in their tissue distribution, these factors have protein structures that classify them as members of four distinct groups of regulators, none of which is found exclusively in the liver (HNF-1, homeo domain; C/EBP, leucine zipper; HNF-3, unclassified; HNF-4, steroid hormone receptors). Second, we cannot immediately understand the logic that unites the group of genes that a particular factor may help regulate. For example, HNF-4 apparently acts positively on genes encoding apolipoproteins, which are involved in cholesterol homeostasis, transthyretin, which carries thyroid hormone and Vitamin A in the serum, as well as α1-antitrypsin, a protease inhibitor, pyruvate kinase, which plays a role in glycolysis, and glutamine synthetase, which acts in amino acid biosynthesis (C. F. Kuo, F. M. Sladek, unpublished observations). Why this factor is involved in regulating this varied assortment of genes is far from obvious.

The invention has been described in detail, setting forth the preferred embodiments. However, alternative embodiments are contemplated as falling within the invention. Consequently, the scope of the claims is not to be limited by the teachings contained herein.

What is claimed is:

1. An isolated DNA molecule comprising nucleotides 59-1171 of the cDNA sequence of FIG. 3B (SEQ ID NO:1).

2. A unicellular host transformed with the DNA molecule comprising the cDNA sequence of claim 1.

3. A unicellular host according to claim 2, wherein said DNA molecule is operatively linked to an expression control sequence selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase, the promoters of acid phosphatase and the promoters of the yeast α-mating factors.

4. A method for producing HNF-4 comprising the step of culturing a transformed host according to claim 2.

5. A DNA molecule according to claim 1 wherein said DNA sequence is produced by recombinant means and is operatively linked to an expression control sequence.

6. The recombinant DNA molecule of claim 5, wherein said expression control sequence is selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase, the promoters of acid phosphatase and the promoters of the yeast α-mating factor.

7. The DNA molecule of claim 1 wherein said DNA sequence is operatively linked to a promoter and a reporter sequence.

8. A viral construct containing the cDNA sequence of FIG. 3B (SEQ ID NO. 1).

9. An isolated DNA molecule comprising a sequence, selected from the group consisting of:

(A) nucleotides 59-1171 of the DNA sequence of FIG. 3B (SEQ ID NO:1);

(B) DNA sequences that encode an amino acid sequence encoded by the DNA sequence of (A); and (C) DNA sequences which are complementary to the DNA sequences of (A) or (B).

10. An isolated DNA molecule comprising a replicon and the DNA sequence of claim 9.

11. A recombinant DNA molecule comprising a DNA sequence, selected from the group consisting of:

(A) nucleotides 59-1171 of the DNA sequence of FIG. 3B (SEQ ID NO:1);

(B) DNA sequences that encode an amino acid sequence encoded by the DNA sequence of (A); and (C) DNA sequences which are complementary to the DNA sequences of (A) or (B).

12. The DNA molecule of either of claims 9 or 11, wherein said DNA sequence is operatively linked to an expression control sequence.

13. The DNA molecule of claim 12, wherein said expression control sequence is selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase, the promoters of acid phosphatase and the promoters of the yeast α-mating factors.

14. An expression vector comprising a nucleotide sequence selected from the following:

(A) nucleotides 59-1171 of the DNA sequence of FIG. 3B (SEQ ID NO:1);

(B) DNA sequences that encode an amino acid sequence encoded by the DNA sequence of (A); and (C) DNA sequences which are complementary to the DNA sequences of (A) or (B)

in the sense or antisense direction.

15. The expression vector of claim 14 cotransfected into a host cell with a reporter construct and a promoter element.

16. A unicellular host transformed with a recombinant DNA molecule comprising a DNA sequence, selected from the group consisting of:

(A) nucleotides 59-1171 of the DNA sequence of FIG. 3B (SEQ ID NO:1);

(B) DNA sequences that encode an amino acid sequence encoded by the DNA sequence of (A); and (C) DNA sequences which are complementary to the DNA sequences of (A) or (B);

wherein said DNA sequence is operatively linked to an expression control sequence.

17. The unicellular host of claim 16, wherein said expression control sequence is selected from the group consisting of the early or late promoters of SV40 or adenovirus, the lac system, the trp system, the TAC system, the TRC system, the major operator and promoter regions of phage λ, the control regions of fd coat protein, the promoter for 3-phosphoglycerate kinase, the promoters of acid phosphatase and the promoters of the yeast α-mating factors.

18. The unicellular host of claim 16 wherein the unicellular host is selected from the group consisting of E. coli, Pseudomonas, Bacillus, Streptomyces, yeasts, CHO, R1.1, B-W, L-M, COS 1, COS 7, BSC1, BSC40, and BMT10 cells, plant cells, insect cells, and human cells in tissue culture.

19. A method for producing HNF-4 comprising culturing the transformed host of claim 16.

20. An isolated DNA molecule comprising nucleotides 59-1171 of the cDNA sequence of FIG. 3B (SEQ. ID. NO:1) under the control of transcriptional and translational control sequences which are capable of effecting the expression of said coding sequence in a host cell, wherein at least one of said transcriptional and translational control sequences is heterologous to said coding sequence.

21. The DNA molecule of claim 20 wherein said coding sequence is uninterrupted by introns.

22. A composition of cells transformed by the DNA molecule of claim 20 substantially free of cells that are not transformed by said DNA molecule.

23. The cells of 22 which are prokaryotic cells.

24. The cells of claim 22 which are eukaryotic cells.

25. The cells of claim 22 which are mammalian cells.

26. A method for producing HNF-4 which comprises culturing the composition of cells transformed by a DNA molecule according to claim 20 under conditions whereby said HNF-4 is expressed, and recovering the expressed HNF-4.

27. The method of claim 26 wherein said cells are prokaryotic.

28. The method of claim 26 wherein said cells are eukaryotic.

29. The method of claim 26 wherein said cells are yeast.

* * * * *

UNITED STATES PATENT AND TRADEMARK OFFICE
CERTIFICATE OF CORRECTION

PATENT NO. : 5,604,115
DATED     : February 18, 1997
INVENTOR(S) : Frances M. Sladek et al It is certified that error appears in the above-identified patent and that said Letters Patent is hereby corrected as shown below:

On the cover page of the Patent, insert related U. S. Application Data, to read as follows: -- [63] National filing of PCT/US91/09733, filed December 23, 1991, which is a PCT filing of U.S.Serial No. 07/631,720, filed December 21, 1990, now abandoned:

Column 1, line 3, insert the following to read as:-- National filing of PCT/US91/09733, filed December 23, 1991, which is a PCT filing of U.S.Serial No. 07/631,720, filed December 21, 1990, now abandoned, the disclosures of which are hereby incorporatedby reference in their entireties.

Signed and Sealed this

Ninth Day of December, 1997

Attest:

BRUCE LEHMAN

Attesting Officer

Commissioner of Patents and Trademarks